United States Patent [19]

Voorhees et al.

[11] 4,302,457

[45] Nov. 24, 1981

[54] PROCESS FOR THERAPEUTIC TREATMENT

[75] Inventors: John J. Voorhees, Ann Arbor; Wendell Wierenga, Kalamazoo, both of Mich.

[73] Assignees: The Upjohn Company, Kalamazoo; The Regents of the University of Michigan, Ann Arbor, both of Mich.

[21] Appl. No.: 174,991

[22] Filed: Aug. 4, 1980

Related U.S. Application Data

[62] Division of Ser. No. 787,230, Apr. 13, 1977, Pat. No. 4,235,887.

[51] Int. Cl.³ .................... A61K 31/705; C07J 41/00; A61K 31/505
[52] U.S. Cl. .................................. 424/251; 424/180; 424/309; 424/311; 424/330; 424/301; 424/329; 424/252; 424/308; 424/324; 424/274; 424/267; 424/279; 260/397.45
[58] Field of Search .......................................... 424/251

[56] References Cited

U.S. PATENT DOCUMENTS

| | | | |
|---|---|---|---|
| 4,162,316 | 7/1979 | Nishimura et al. | 424/250 |
| 4,166,116 | 8/1979 | Coutts et al. | 424/250 |
| 4,224,325 | 9/1980 | Szilagyi et al. | 424/250 |

*Primary Examiner*—Elbert L. Roberts
*Attorney, Agent, or Firm*—John J. Killinger

[57] ABSTRACT

This invention relates to a new method of therapy comprising the administration of a pro-drug to a human or animal, said pro-drug being a compound formed by a therapeutic compound chemically combined with another moiety by a photocleavable bond and irradiating the diseased area with ultraviolet radiation in an amount sufficient to cleave the bond and release the therapeutic compound in a therapeutically effective amount. Specifically disclosed are pro-drugs which are cleaved to therapeutically active medications which are anti-proliferative and anti-inflammatory compounds and the treatment of inflammatory and/or proliferative skin diseases therewith.

1 Claim, No Drawings

PROCESS FOR THERAPEUTIC TREATMENT

CROSS REFERENCE TO RELATED APPLICATIONS

This application is a division of application Ser. No. 787,230, filed Apr. 13, 1977, now U.S. Pat. No. 4,235,887, issued Nov. 25, 1980.

BRIEF DESCRIPTION OF THE INVENTION

This invention relates to a method of therapeutic treatment in a localized area in which an inactive form of a drug is administered systemically and thereby exhibits diminished or no pharmacological activity until at the site of the desired action the therapeutically active form of the drug is released by irradiation.

BACKGROUND OF THE INVENTION

In recent years proliferative skin diseases have been treated successfully to alleviate such diseases by certain types of therapeutically active compounds administered in association with a pharmaceutical carrier. The expression "proliferative skin diseases" has developed an art-accepted meaning, namely, benign and malignant inflammatory and/or proliferative skin diseases which are characterized by accelerated cell division in the epithelium of the skin (epidermis) and the support tissues of the skin (dermis) or appendages thereto, and which are associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyper-keratosis, premalignant sun-induced keratosis, non-malignant keratosis, acne, and seborrheic dermatitis in humans and atopic dermatitis and mange in domesticated animals.

Active compounds capable of alleviating a skin proliferative disease have typically been applied as a composition including a pharmaceutical carrier either topically, orally, injection, intra-dermally, intra- or peri-lesionally or subcutaneously. Certain of these therapeutically active compositions are most effective when applied topically while others work better when applied systemically, either orally or by injection. On the other hand, certain of the compounds penetrate the skin only with great difficulty and are difficult to use effectively when applied topically; other of such compositions which are capable of alleviating an inflammatory and/or proliferative skin disease when administered systemically are medically unacceptable because of the adverse pharmacological reactions which result from the administration of a dosage sufficiently large to alleviate such disease. It has, therefore, become recognized that there is a substantial problem of providing the necessary quantity of the therapeutically active material at the site of the lesion, or other representation of such inflammatory and/or proliferative skin diseases, with many of the compositions which are therapeutically capable of alleviating such disease and concurrently avoiding adverse systemic side reactions. This invention provides a solution to the problem of continuously providing at the desired site the needed quantity of at least one therapeutically active composition while simultaneously overcoming the previously encountered problems with certain compositions of skin penetration and/or medically unacceptable toxicity to the system when systemically administered.

DETAILED DESCRIPTION OF THE INVENTION

The present invention provides a process which enables the administration of a single compound or mixture of compounds which have been preliminarily altered chemically to produce a pro-drug, that is, a modified form of an otherwise therapeutically active compound; as the result of the chemical alteration, the pro-drug has diminished, little or no therapeutic or pharmacologic activity until that pro-drug is exposed to irradiation at the desired site of alleviation of an inflammatory and/or proliferative disease. The irradiation releases the therapeutically active form of the compound or compounds at the irradiated site only and the released compound, or mixture, of compounds, function to alleviate the inflammatory and/or proliferative skin disease.

As used in the present specification and claims the term "pro-drug" means a therapeutic compound or compounds which have been altered chemically to include a group or groups which substantially inactivate the therapeutic capability of alleviating an inflammatory and/or proliferative skin disease and, prior to cleavage, substantially eliminates undesirable pharmacological properties which may otherwise be present. The attachment, or chemical bond, between the cleavable group and the therapeutically active portion of the pro-drug, is one which is susceptible to cleavage by radiation with ultraviolet light, but one which substantially resists cleavage by enzymatic or metabolic action in the body. The cleaved group or fragment itself is non-toxic, that is, the cleaved group exhibits at most a small but medically acceptable degree of toxicity in the quantities present as a result of the cleavage; the cleaved group may itself be therapeutically active and after cleavage function to aid the alleviation either additively or preferably synergistically, with the other portion of the cleaved pro-drug.

The method of this invention is useful with any and all therapeutically active compounds which are capable of alleviating an inflammatory and/or proliferative skin disease when administered by the ordinary methods of application, even though such compounds exhibit no particular problem of skin penetration to thereby prevent successful topical use or exhibit less than medically unacceptable systemic side effects. In such cases, the method of this invention is nevertheless advantageous because it permits the administration of smaller quantities of the therapeutically active compounds and provides an effective, easy to control and desirable manner of securing maximum alleviation of inflammatory and/or proliferative skin diseases. However, the greatest utility of the process of this invention resides in its ability to render useful many compounds which, although therapeutically sufficiently active to alleviate an inflammatory and/or proliferative skin disease may, nevertheless, be unusable because of their medically unacceptable cumulative systemic side effects.

Therapeutically active compounds which are capable of alleviating an inflammatory and/or proliferative skin disease and which are suitable for converting into pro-drugs useful in the process of this invention from which release of said therapeutically active compound upon irradiation will occur include those drugs containing derivatizable functional group such as hydroxyl, sulfhydryl, primary and secondary amino and amido, carboxyl, carbonyl, 1,2- and 1,3-dihydroxy groups capable of forming acetals, and combinations thereof. It is, however, not required for the practice of this invention that the pro-drug be chemically derived directly from a therapeutically active compound as chemically equivalent alternatives well known to one skilled in the art may be used and, may, in some instances be preferred.

Therapeutically active compounds and chemically equivalent alternatives suitable for the preparation of pro-drugs of this invention may thus be characterized as follows:

A.  Drug—ZH
A'. Drug—Y
B.  Drug—CO₂H
C.  Drug—CONH—
D.  Drug—CO—
E.
$$\text{Drug}-\overset{|}{\text{C}}(\text{OH})-\overset{|}{\underset{|}{\text{C}}}-\text{OH} \text{ and}$$

$$\text{Drug}-\overset{|}{\text{C}}(\text{OH})-\text{C}-\text{C}-\text{OH}$$

wherein Z is O, S, and N—; — is a connecting bond to some portion of the therapeutically active compound (drug) or its chemically equivalent alternative; and Y is a leaving group such as Cl, Br, I, sulfonate ester (e.g., mesylate, tosylate) and the like.

The therapeutically active compounds and chemically equivalent alternatives useful in this invention are converted into pro-drugs by reaction with a reagent by methods both known in the art and further described below. Suitable reagents include:

(a) ArCH₂Y
(b) ArCH₂OH
(c) ArNH₂
(d) ArCHO
(e) ArCH(OH)CH₂OH
(f) ArCH₂OCOCl
(g)

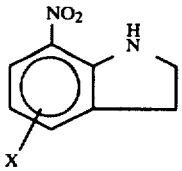

wherein Ar is

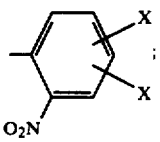

X is H, methoxy, chloro and bromo; and Y is a leaving group such as Cl, Br, I, sulfonate ester (e.g., mesylate, tosylate) and the like.

Pro-drugs of this invention characterized as indicated below, may be prepared by reaction of the therapeutically active compound (represented by a capital letter, A-E) or a chemically equivalent alternative (A') with a reagent (represented by a small letter a-g):

| Pro-Drug | Prepared by reaction of |
|---|---|
| Drug—Z—CH₂Ar | A + a; A' + b |
| Drug—Z—CO₂CH₂Ar | A + f |
| Drug—CONHAr | B + c; C + a |
| Drug—CO₂CH₂Ar | B + a; B + b |
| Drug—C(—O—)(—O—)Ar | D + e |
| Drug—C(—O—)(—C—O—)Ar | E + d |
| Drug—C(O—Ar)(—C—O—C—) | E + d |
| Drug CON-(aryl with NO₂ and X) | B + g | by procedures described in more detail below.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and the claims hereof, psoriasis is alleviated when a scale-free psoriasis lesion is noticeably decreased in thickness, or noticeably but incompletely cleared or completely cleared.

Specific illustrative embodiments of this invention comprise a pharmaceutical carrier and about 0.1 to 15% w/w of one or more of the compounds selected from the following groups. In the illustrations the formulae designated "b" are the pro-drug of the invention and the formulae "a" represent the starting material for preparing the drug.

1. A compound of the formula Ib:

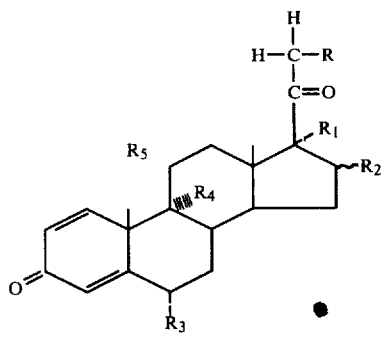

a. R is OH, Cl, or Br; $R_1$ is hydrogen or hydroxy, acyloxy wherein acyl is 2 to 8 carbon atoms; $R_2$ is hydrogen, hydroxy, methyl, fluoro or chloro; and $R_1$ and $R_2$ taken together can be

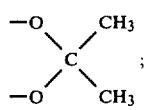

$R_3$ is hydrogen, methyl, chloro, or fluoro; $R_4$ is hydrogen, chloro or fluoro; $R_5$ is oxygen, β-hydroxy or β-chloro, with the proviso that when $R_5$ is β-chloro then $R_4$ must be chloro.

b. $R_1$, $R_2$, $R_3$, $R_4$, and $R_5$ are as defined above and R is

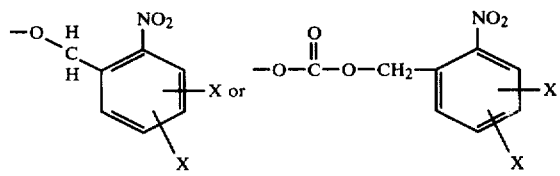

wherein X is H, methoxy, bromine or chloro;

2. A compound of the formula IIb.

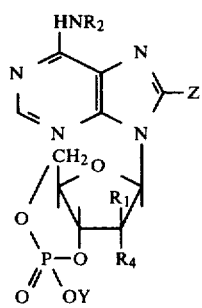

a. $R_1$ and $R_4$ are selected from hydrogen and OR with the proviso that only one of $R_1$ and $R_4$ can be OR; $R_2$ is R, butyryl or

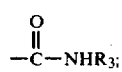

$R_3$ is phenyl, benzyl or alkyl of 1-8 carbon atoms; Y is H or alkali metal; Z is H, benzylthio, or alkylthio wherein alkyl is of 1-8 carbon atoms, inclusive; and R is H.

b. $R_1$, $R_2$, $R_3$, $R_4$ and Z are as defined above; R is H,

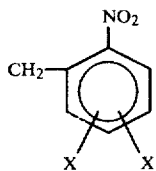

or

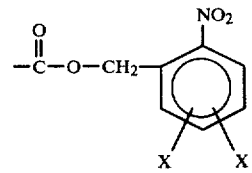

and Y is H or

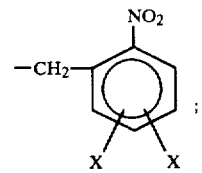

provided that at least one of the groups R and Y is not H; and X is H, methoxy, chloro and bromo.

3. A compound of the formula IIIb.

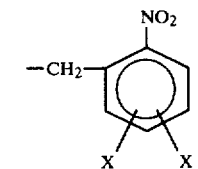

a. $R_1$ is —$CONH_2$, —$CSNH_2$, —$C(NH)NH_2$, —CN, or —$CO_2CH_3$; $R_2$ and $R_3$ are H and OR with the proviso that only one of $R_2$ and $R_3$ can be OR; Y is H or alkali-metal; and R is H.

b. $R_1$, $R_2$, and $R_3$ are as defined above; R is H,

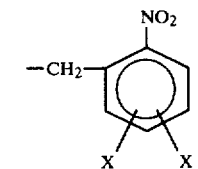

or

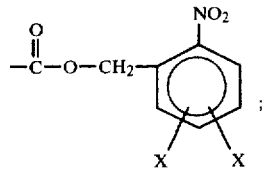

and Y is H or

-continued

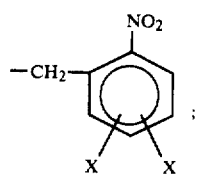

provided that one of the groups R and Y is not H; and X is H, methoxy, chloro, or bromo.

4. A compound of the formula IVb:

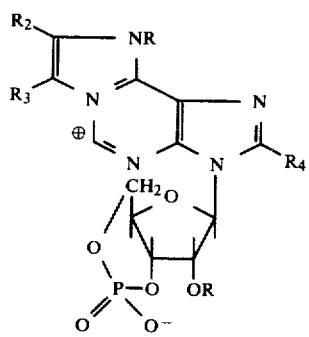
IVa,b a. $R_2$ is H or phenyl; $R_3$ is propyl, isopropyl, or phenyl; $R_4$ is H, bromo, methylthio, or benzylthio; and R is H.

b. $R_2$, $R_3$, and $R_4$ are as defined above; R is H,

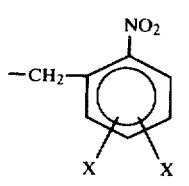

or

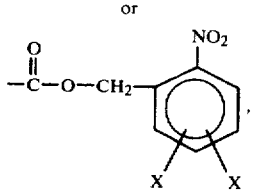

provided that at least one of the groups R is not H; and X is H, methoxy, chloro and bromo.

5. A compound of the formula Vb:

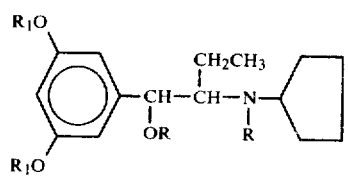
Va,b a. R is H; and $R_1$ is H or acyl of an aliphatic carboxylic acid from 2–5 carbon atoms.

b. R is selected from the groups H,

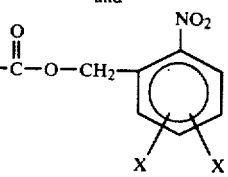
and

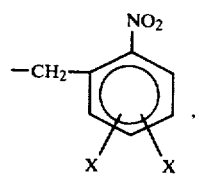

and $R_1$ is selected from the groups H, acyl of an aliphatic carboxylic acid of from 2–5 carbon atoms and B

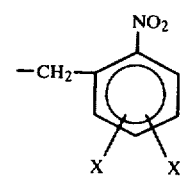

provided that at least one of the groups R and $R_1$ is

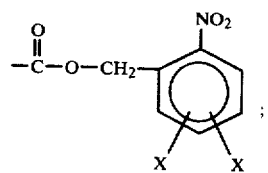

or

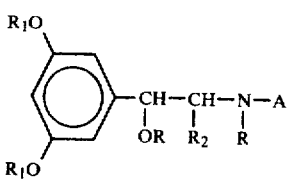

and X is selected from hydrogen, methoxy, chloro, and bromo.

6. A compound of the formula VIb:

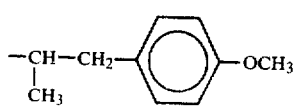
VIa,b a. R is H; $R_1$ is selected from H and acyl of an aliphatic carboxylic acid of from 2–5 carbon atoms, inclusive; $R_2$ is selected from H and alkyl of 1–4 carbon atoms; and A is selected from:

—CH—CH$_2$—⟨phenyl⟩—OCH$_3$
|
CH$_3$

-continued

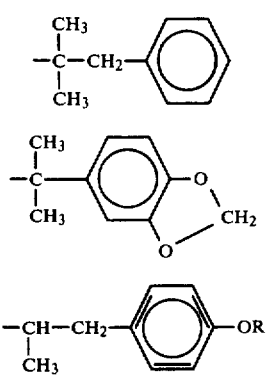

b. R is H, Y or

$R_1$ is H, Y and acyl of an aliphatic carboxylic acid of from 2-5 carbon atoms, inclusive; $R_2$ and A are as defined above, Y is

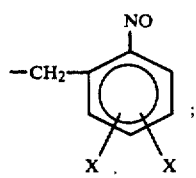

and X is H, methoxy, chloro and bromo, provided that at least one of the groups R and $R_1$ is Y or

7. A compound of the formula VIIb:

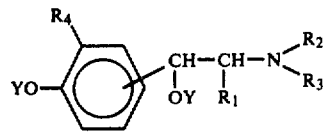
VIIa,b a. $R_1$ is H or alkyl of from 1 to 6 carbon atoms; $R_2$ is Y or benzyl; $R_3$ is Y, alkyl of from 1 to 6 carbon atoms or YO— or YNH— substituted forms thereof or a heterocyclic residue, cycloalkyl, aralkyl, or aryloxyalkyl or alkoxy-substituted forms thereof; $R_4$ is YO, YO-substituted alkyl of from 1 to 6 carbon atoms, YO-substituted aralkyl, —$CO_2$-alkyl, or amide of the formula —$CONR_5R_6$, where $R_5$ and $R_6$ are H, alkyl of from 1 to 6 carbon atoms, or $NR_5R_6$ forms a heterocyclic ring; and Y is H.

b. $R_1$, $R_2$, $R_3$, $R_4$, $R_5$ and $R_6$ are as defined above; Y is selected from the groups H,

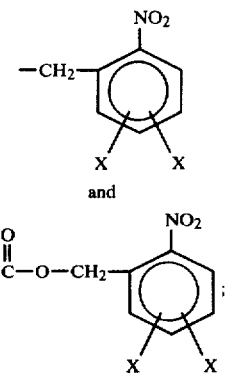

and X is H, methoxy, chloro and bromo provided that at least one of the groups Y is not H.

8. A compound of the formula VIIIb:

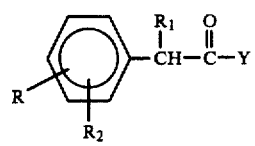
VIIIa,b a. R is alkyl of 1-6 carbon atoms, phenyl, substituted phenyl, cycloalkyl, alkoxy, or phenoxy; $R_1$ is H or alkyl of 1-4 carbon atoms; $R_2$ is selected from H, alkyl of 1-3 carbon atoms, inclusive, Cl, Br, or F; and Y is OH.

b. R, $R_1$ and $R_2$ are as defined above and Y is selected from

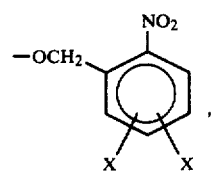

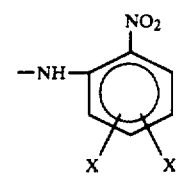

and

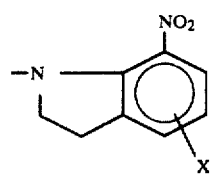

and X is H, methoxy, chloro, or bromo,

9. A compound of the formula IXb:

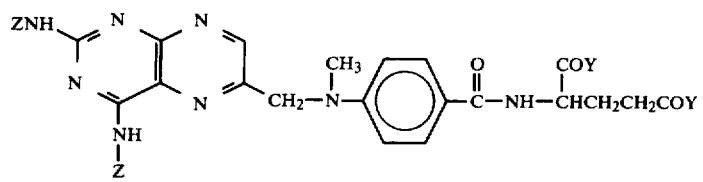

IXa,b a. Z is H; Y is OH.
b. Z is selected from H,

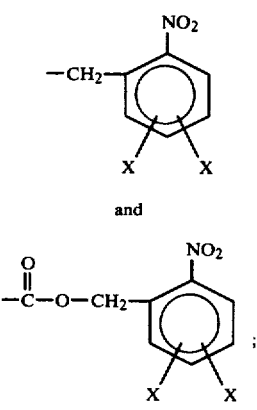

Y is selected from OH,

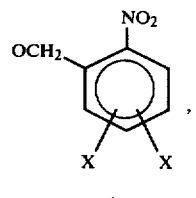

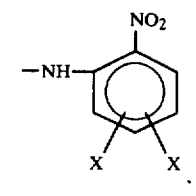

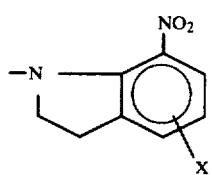

wherein X is selected from H, methoxy, chloro, and bromo, provided that at least one of the groups Y is not OH when Z is H and at least one of the groups Z is not H when Y is OH.

10. A compound of the formula Xb:

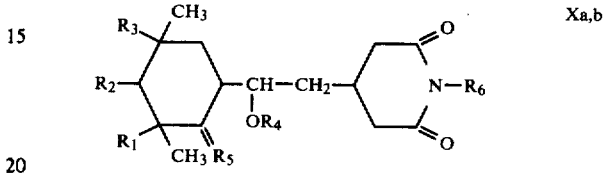

a. $R_1$, $R_2$ and $R_3$ selected from the group H, hydroxyl, and acetoxyl, provided that not more than one of the groups $R_1$, $R_2$ and $R_3$ is hydroxyl or acetoxyl; $R_4$ and $R_6$ are H; and $R_5$ is carbonyl.

b. $R_1$ and $R_3$ are as defined above; $R_2$ is selected from the group H, —OY, and acetoxyl provided that not more than one of the groups $R_1$, $R_2$ and $R_3$ is OH, OY or acetoxyl; $R_4$ is selected from the group H and Y; Y is

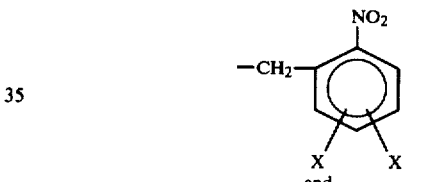

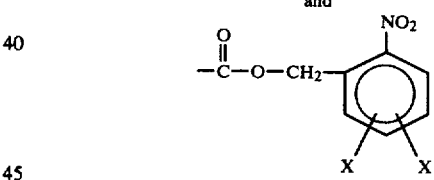

$R_5$ is selected from the group carbonyl and

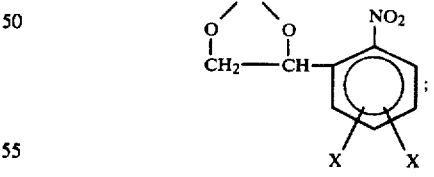

$R_6$ is selected from the group H and

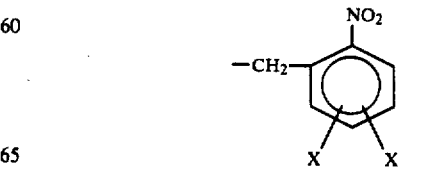

and X is H, methoxy, chloro and bromo, provided that at least one of the groups, $R_2$, $R_4$ and $R_6$ is

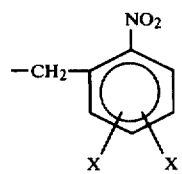
or
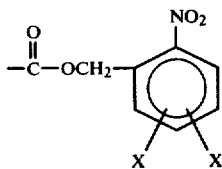
when R₅ is carbonyl.
11. A compound of the formula XIb:
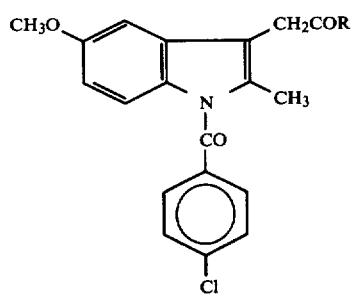    XIa,b
a. R is OH.
b. R is
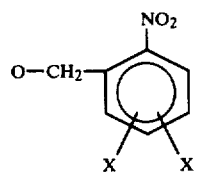
and
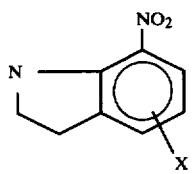
wherein X is selected from H, methoxy, bromo, and chloro.
12. A compound of the formula XIIb:
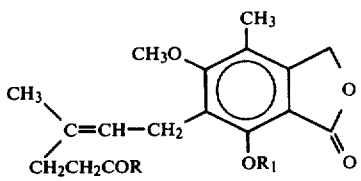    XIIa,b
a. R₁ is H; R is OH.
b. R₁ is H and
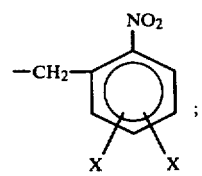  ;
R is —OH,
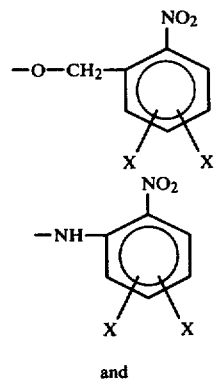
and
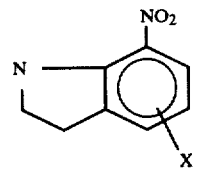
and X is selected from H, methoxy, chloro, and bromo; provided that when R₁ is H, R is not OH.
13. A compound of the formula XIIIb:
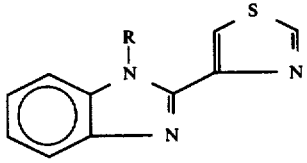    XIIIa,b
a. R is H.
b. R is
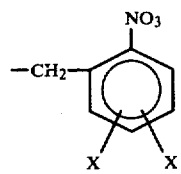
and -continued

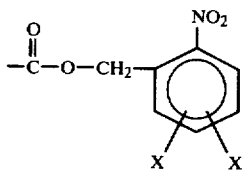

wherein X is selected from H, methoxy, chloro, and bromo.

14. A compound of the formula XIVb:

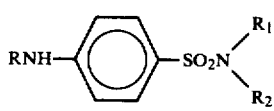   XIVa,b a. R is Y; $R_1$ is selected from H, 2-pyridyl, 2-thiazolyl, 2-pyrimidyl, 4-methylpyrimidyl, and 4,6-dimethylpyrimidyl; $R_2$ is Y, or, together with $R_1$, is guanidyl; and Y is H.

b. R, $R_1$ and $R_2$ are as defined above and Y is selected from the groups H,

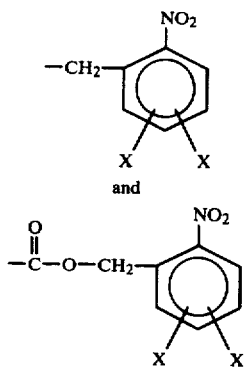

wherein X is H, methoxy, chloro and bromo; provided that at least one of the groups Y is not H.

15. A compound of the formula XVb:

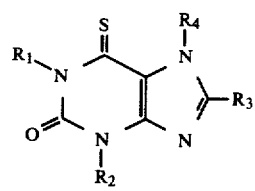   XVa,b a. R and $R_1$ are selected from the groups consisting of Y, alkyl containing 3–7 carbon atoms, cycloalkyl containing 3–7 carbon atoms and aralkyl wherein the alkyl portion contains 1–7 carbon atoms; $R_2$ is Y or alkyl containing 1–4 carbon atoms; $R_3$ is H or SY; and Y is H providing that when $R_3$ is H, one of the groups R, $R_1$ and $R_2$ is H.

b. R, $R_1$, $R_2$ and $R_3$ are defined as above; Y is selected from the group H,

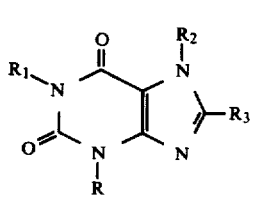

and X is selected from H, methoxy, chloro and bromo; provided that at least one of the groups Y is not H.

16. A compound of the formula XVIb:

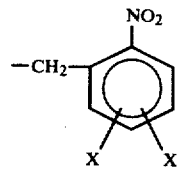   XVIa,b a. $R_1$ is selected from a group consisting of methyl, ethyl, propyl or $-CH_2-CH=CH_2$; $R_2$ is methyl, ethyl, propyl, $-CH_2-CH=CH_2$, isopropyl, isobutyl, $CH_2-C(CH_3)=CH_2$, pentyl, 3-methoxypropyl, 2-methylbutyl, hexyl, benzyl, phenyl, phenethyl or furfuryl; $R_3$ is selected from the group consisting of H, methyl or ethyl; $R_4$ is H.

b. $R_1$, $R_2$ and $R_3$ are as defined above; $R_4$ is

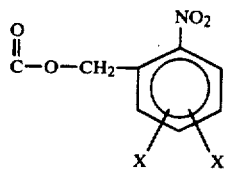

wherein X is H, methoxy, chloro and bromo.

17. A compound of the formula XVIIb:

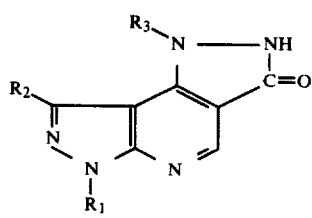   XVIIa,b a. $R_1$ is Y; $R_2$ is selected from the group consisting of H and lower alkyl from 1-3 carbon atoms; $R_3$ is selected from the group Y and lower alkyl from 1-3 carbon atoms; Y is H.

b. $R_1$, $R_2$ and $R_3$ are as defined above; Y is selected from the group H,

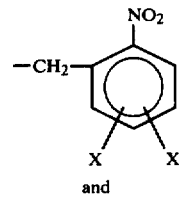

and

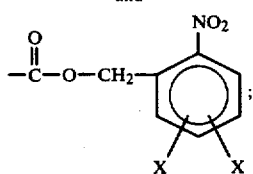

and X is H, methoxy, chloro or bromo; provided that one of the groups Y is

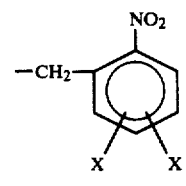

or

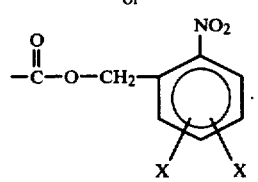

18. A compound of the formula XVIIIb:

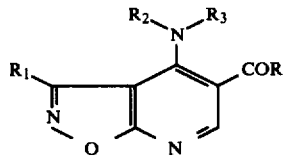

XVIIIa,b a. $R_1$ is selected from the group consisting of H or lower alkyl of 1 to 3 carbon atoms; $R_2$ and $R_3$ are selected from the group consisting of Y, lower alkyl of 1 to 4 carbon atoms, phenyl, benzyl, phenethyl, dialkylaminoalkyl in which alkyl is of 1 to 3 carbon atoms or taken together $R_2$ and $R_3$ form a heterocyclic ring such as pyrrolidino, N-methyl-piperazino, piperidino, methylaziridino and 2,3-dimethylaziridino; R is OH; and Y is H.

b. $R_1$, $R_2$ and $R_3$ are as defined above; Y is selected from the group consisting of H,

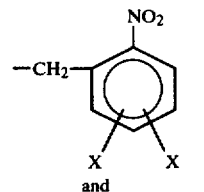

and

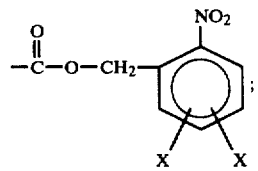

R is selected from the group OH,

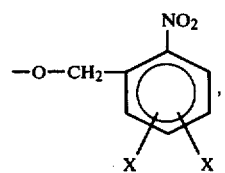

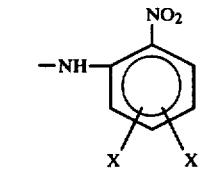

and

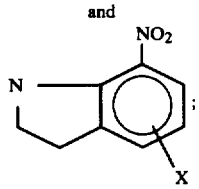

X is H, methoxy, chloro and bromo; provided that when R is OH, one of the groups Y is

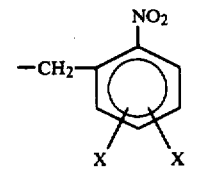

or

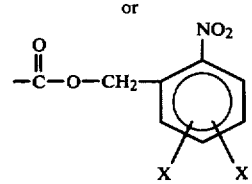

19. A compound of the formula XIXb:

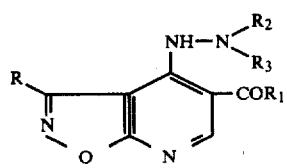

XIXa,b a. R is H, lower alkyl of 1 to 8 carbon atoms, benzyl or phenethyl; $R_2$ is Y, lower alkyl of 1 to 8 carbon atoms or phenyl; $R_3$ is Y, lower alkyl as defined above or lower alkanoyl in which the acyl radical is of 1 to 8 carbon atoms, providing that $R_2$ and $R_3$ are not both H and only one of the groups R, $R_2$ and $R_3$ is a phenyl containing substituent; Y is H, and $R_1$ is OH.

b. R, $R_2$ and $R_3$ are as defined above; Y is selected from the group H,

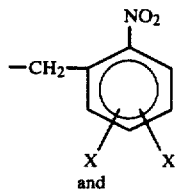
and
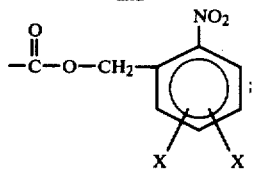

$R_1$ is selected from the group OH,

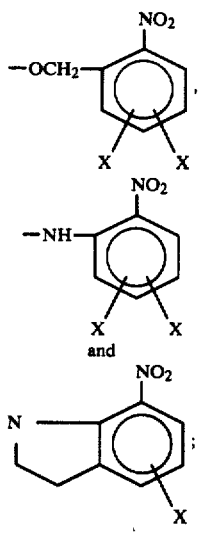

H is H, methoxy, chloro and bromo; and pharmacologically acceptable salts thereof, provided that at least one of the groups Y is

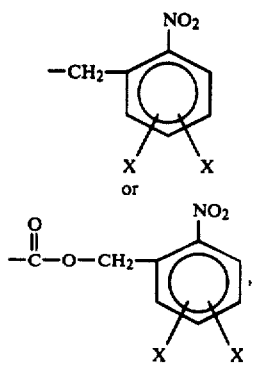

when $R_1$ is OH.

20. A compound of the formula XXb:

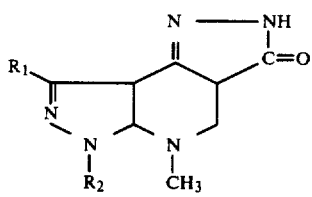

XXa,b a. $R_1$ is lower alkyl of 1-7 carbon atoms, phenyl, benzyl, or phenethyl; $R_2$ is H.

b. $R_1$ is as defined above; $R_2$ is

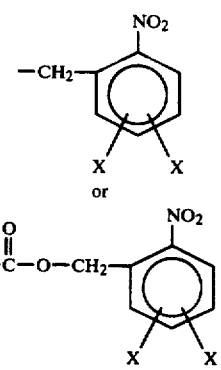

wherein X is H, methoxy, chloro, or bromo.

21. A compound of the formula XXIb:

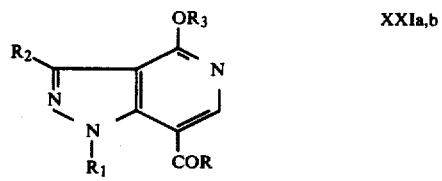

XXIa,b a. $R_1$ is Y, lower alkyl of 1–12 carbon atoms, m- or p-substituted phenyl, benzyl, phenethyl or benzoyl in which the m- or p-substituents are H, halogen, methoxy or methyl; $R_2$ is H, lower alkyl of 1 to 12 carbon atoms, phenyl, benzyl or phenethyl; $R_3$ is lower alkyl of 1 to 12 carbon atoms, benzyl or phenethyl; Y is H and R is OH.

b. $R_1$, $R_2$ and $R_3$ are as defined above; R is selected from the group OH,

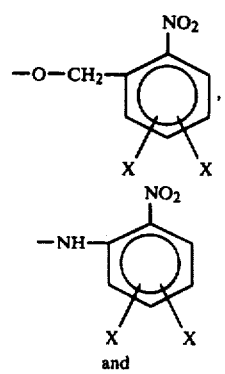
and

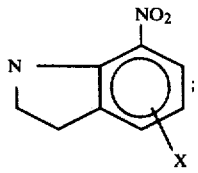

X is H, methoxy, chloro and bromo; and Y is H,

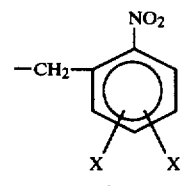

and

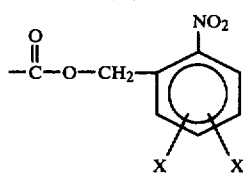

provided that when R is OH, R₁ is Y and Y is

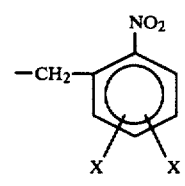

or

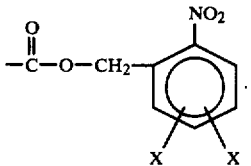

22. A compound of the formula XXIIb:

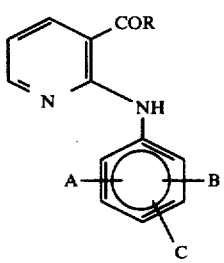

XXIIa,b a. A and B are lower alkyl of from 1-8 carbon atoms, lower alkoxy of from 1-8 carbon atoms, chloro, bromo, or nitro; C is H, lower alkyl of from 1 to 8 carbon atoms, halogen, or —CF₃; and R is OH.

b. A, B and C are as defined above; R is selected from the group

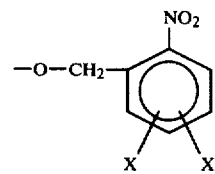

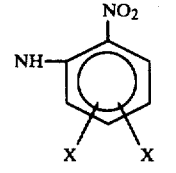

and

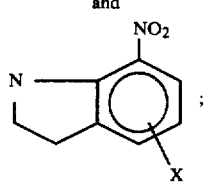

X is H, methoxy, chloro and bromo.

23. A compound of the formula XXIIIb:

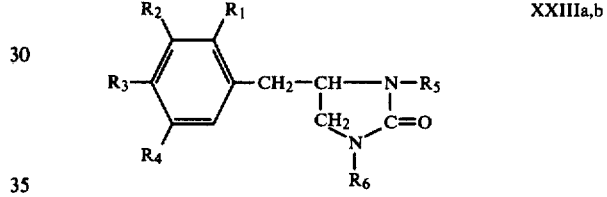

XXIIIa,b a. $R_1$ is H, halogen, lower alkyl of from 1 to 6 carbon atoms; $R_2$, $R_3$ and $R_4$ taken independently of each other are H, lower alkyl and lower alkoxy and provided that $R_2$, $R_3$ and $R_4$ taken independently of each other represent at least one oxygenated substituent; or $R_1$, $R_2$, $R_3$ and $R_4$ taken as an adjacent pair is methylenedioxy; $R_5$ and $R_6$ are H; and the optical antipodes thereof.

b. $R_1$, $R_2$, $R_3$ and $R_4$ are as defined above; $R_5$ and $R_6$ are selected from the group H and

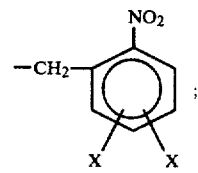

and X is H, methoxy, chloro, and bromo, provided that at least one of the groups $R_5$ and $R_6$ is not H.

24. A compound of the formula XXIVb:

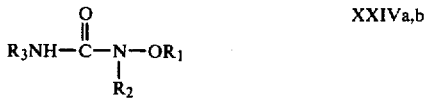

XXIVa,b a. $R_1$, $R_2$ and $R_3$ are H.

b. $R_1$ is selected from the group H and

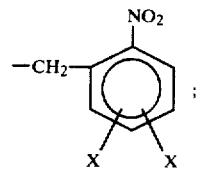

$R_2$ and $R_3$ are selected from the group H,

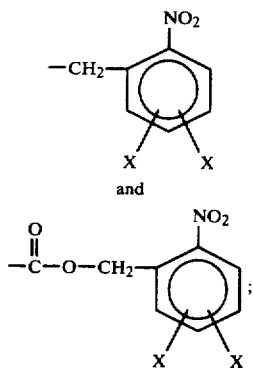

and X is H, methoxy, chloro and bromo, provided that at least one of the groups $R_1$, $R_2$ and $R_3$ is not H.

25. A compound of the formula XXVb:

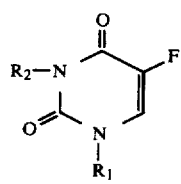

XXVa,b a. $R_1$ and $R_2$ are H.
b. $R_1$ and $R_2$ are selected from the group H and

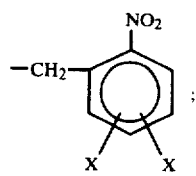

X is H, methoxy, chloro and bromo, provided that one of the groups $R_1$ and $R_2$ is not H.

26. A compound of the formula XXVIb:

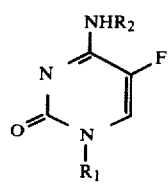

XXVIa,b a. $R_1$ and $R_2$ are H.
b. $R_1$ is H or

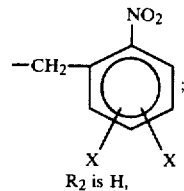

$R_2$ is H, and X is H, methoxy, chloro and bromo, provided that one of the groups $R_1$ and $R_2$ is not H.

27. A compound of the formula XXVIIb:

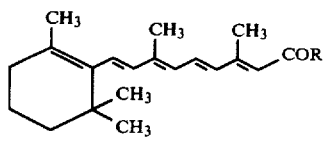

XXVIIa,b a. R is OH.
b. R is selected from the group

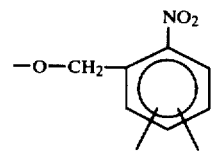

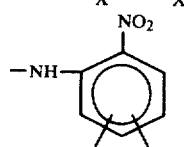

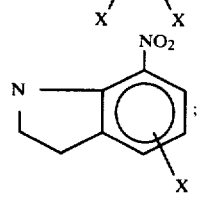

and X is H, methoxy, chloro and bromo.

28. A compound of the formula XXVIIIb:

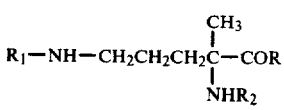

XXVIIIa,b a. $R_1$ and $R_2$ are H; R is OH and $OCH_3$.
b. R is selected from the group OH, $OCH_3$,

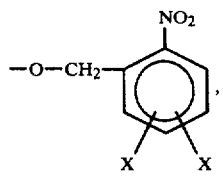

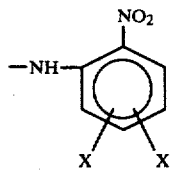

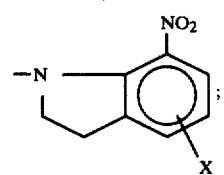

$R_1$ and $R_2$ are selected from the groups H,

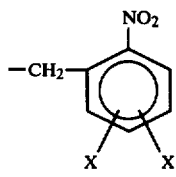

and

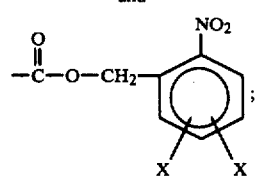

and X is H, methoxy, chloro and bromo, provided that when R is OH or $OCH_3$ at least one of the groups $R_1$ and $R_2$ is not H.

29. A compound of the formula XXIXb:

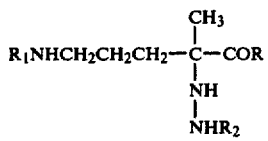

a. $R_1$ and $R_2$ are H; R is OH and $OCH_3$. b. $R_1$ and $R_2$ are selected from the group H,

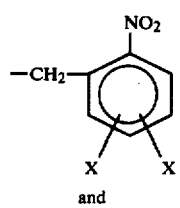

and

-continued

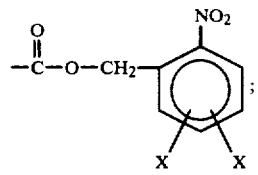

R is selected from the group OH, $OCH_3$,

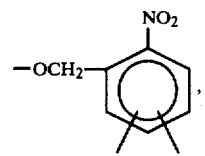

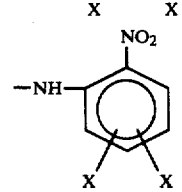

and

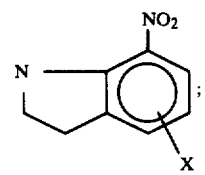

and X is H, methoxy, chloro, and bromo, provided that when R is OH or $OCH_3$, at least one of the groups $R_1$ and $R_2$ is not H.

30. A compound of the formula XXXb:

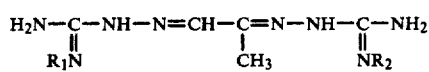 XXXa,b a. $R_1$ and $R_2$ are H.
b. $R_1$ and $R_2$ are selected from the group H,

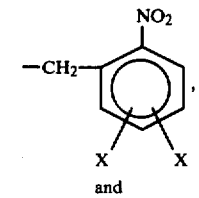

and

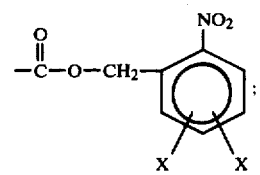

X is H, methoxy, chloro and bromo, provided that one of the groups $R_1$ and $R_2$ is not H.

31. A compound of the formula XXXIb:

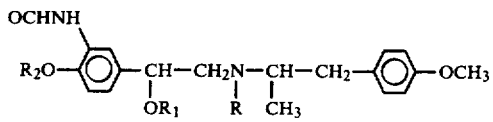 XXXIa,b a. where R, $R_1$ and $R_2$ are H.
b. where R and $R_1$ are selected from H,

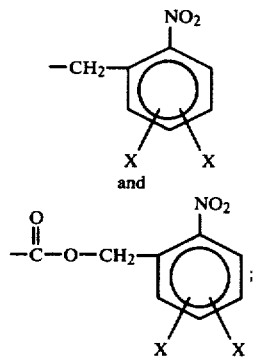

and $R_2$ is selected from H and

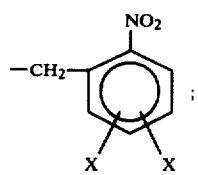

where X is H, methoxy, chloro, and bromo, provided that at least one of the groups R, $R_1$ and $R_2$ is not H.

Compounds of the formulas Ib–XXXIb are prepared by reacting a therapeutically active compound (represented as A–E) or a chemically equivalent alternative (A') with a reagent (represented by a–g) by methods both known in the art and as further exemplified below.

Procedure 1

Reaction of A with reagent a to produce pro-drug Drug-Z-CH$_2$Ar.

To Drug-ZH (A, 5 mmole) in 25 ml. of a polar, aprotic solvent such as dimethylformamide (DMF), tetrahydrofuran (THF), dioxane, and the like under $N_2$ is added, with stirring, 20 mmole of ArCH$_2$Y (a), 5.5 mmoles of a base and/or halogen scavenger such as sodium hydride or silver oxide and 5 mmole of a tertiary amine such as N-N-diisopropylethylamine. The reaction may be heated to effect more rapid reaction as determined by thin layer chromatographic (TLC) monitoring of the reaction mixture. The products are isolated by the addition of ethyl acetate and brine followed by separation of the organic phase, drying, and concentrating in vacuo to give a residue. The residue is chromatographed on silica gel or other suitable chromatographic adsorbents to yield the desired products as determined by NMR and IR identification of the eluted fractions.

Procedure 2

Reaction of A' with reagent b to produce pro-drug Drug-Z-CH$_2$Ar.

This procedure is the same as procedure 1 but A' (Drug-Y) is substituted for A and reagent b is substituted for a.

Procedure 3

Reaction of C with reagent a to produce pro-drug Drug-CONHAr.

This procedure is the same as procedure 1 but C

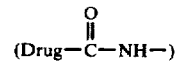

is substituted for A.

Procedure 4

Reaction of B with reagent a to produce pro-drug Drug-CO$_2$CH$_2$Ar.

This procedure is the same as procedure 1 but B (Drug-CO$_2$H) is substituted for A.

Procedure 5

Reaction of A with reagent f to produce

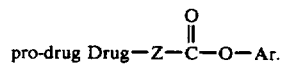

To Drug-ZH (A, 5 mmole) in 50 ml. of dry pyridine at room temperature under $N_2$ is added, with strring, ArCH$_2$OCOCl (f, 7 mmole) in several portions. The reaction may be heated to effect more rapid reaction as determined by thin-layer chromatographic monitoring of the reaction mixture. The products are isolated by addition of ethyl acetate and water, separation, drying, and concentrating the organic phase to dryness. Purification of the desired products is effected by conventional techniques such as chromatography, recrystallization, and the like as identified by standard spectral techniques such as NMR, IR and mass spectrometry.

Procedure 6

Reaction of B with reagents c and g to produce pro-drug Drug-CONHAr and

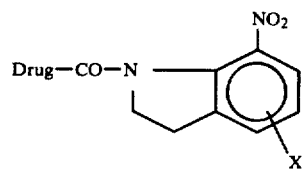

To 5 mmole of Drug-CO$_2$H (B) in 20 ml. of dry pyridine (or DMF and triethylamine) under $N_2$ at room temperature is added, with stirring, 5.5 mmole of an activating agent such as ethyl chloroformate, diimidazole carbonyl, diethyl chlorophosphate, dicyclohexylcarbodiimide and the like. After 1 hour 5.5 mmole of ArNH$_2$ (c) is added. The reaction may be heated to effect a reasonable reaction rate as determined by TLC monitoring of the reaction mixture. The products are isolated by addition of an organic solvent such as ethyl acetate or methylene chloride with water, separation, drying, and evaporation in vacuo of the organic phase to yield a residue. The desired products are purified by conventional purification techniques such as chromatography, recrystallization and the like, and identity determined by spectral techniques such as NMR, IR and mass spectrometry.

Substitution of

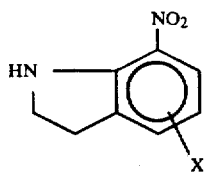

for ArNH₂ affords the corresponding pro-drug,

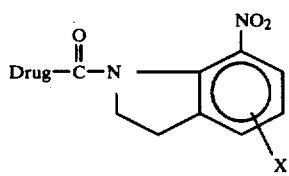

Procedure 7

Reaction of B with reagent b to produce pro-drug Drug-Co₂CH₂Ar.

This procedure is the same as procedure 6, but 2 equivalents of reagent b is substituted for 1 equivalent of reagents c or g.

In like manner, the sodium salt of reagent b may be used instead of reagent b.

Procedure 8

Reaction of D with reagent e to produce pro-drug

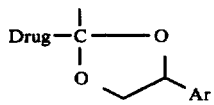

to 5 mmole of

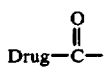 (D)

in benzene is added under N₂ a catalytic amount of an acid such as p-toluenesulfonic acid and 10 mmole of ArCHOHCH₂OH (reagent e). The mixture is refluxed under a Dean-Stark adapter to remove water or through a Soxhlet extractor containing a drying agent such as anhydrous magnesium or sodium sulfate. Other aprotic, non-basic solvents which have a suitable azeotropic ratio with water such as toluene, methylene chloride, and the like may be substituted for benzene. The reaction is monitored at intervals by TLC to determine the extent of ketalization until the reaction is essentially complete. The products are isolated by taking up the reaction mixture in an organic solvent such as methylene chloride or ethyl acetate and washing with saturated sodium bicarbonate, drying the organic phase over sodium sulfate and concentrating in vacuo to yield a residue. The residue is purified by conventional methods such as chromatography, recrystallization, and the like to afford the purified products which are identified by spectral methods such as NMR, IR and mass spectrometry.

Procedure 9

Reaction of E with reagent d to produce pro-drugs

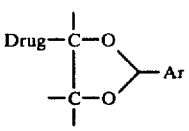

and

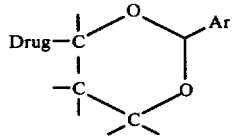

This procedure is the same as procedure 8 but D is replaced E and reagent e is replaced by reagent d.

In procedures 1-9 it is of particular importance to protect the products during their preparation, purification, and storage, from the effects of sunlight and from excessive exposure to fluorescent light inasmuch as the pro-drug products are susceptible to photocleavage.

The above procedures are not to be construed as limiting to a single functional group since some therapeutically active compounds or their chemically equivalent alternatives have more than one reactive functionality, often of different reactivities. It will be clear to one skilled in the art that introduction and removal of suitable protecting groups and appropriate choice of reaction conditions will afford a choice among preferred conditions for maximizing yields of particular products.

Procedure 10

The steroid compounds of the present invention are prepared by reacting compounds of the formula Ib wherein R is hydroxyl, chlorine or bromine with a compound of the formula:

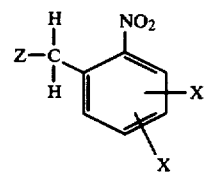

and wherein R is hydroxyl with a compound of the formula:

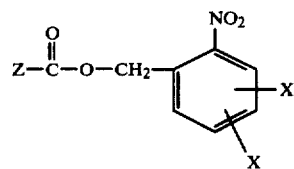

wherein X is methoxy, bromo or chloro and Z is hydroxyl, bromo or chloro provided that when R is hydroxyl then Z is bromo or chloro and when R is bromo or chloro then Z is hydroxyl under an inert atmosphere such as nitrogen in N₂ and in an inert solvent, e.g., dimethylformamide, tetrahydrofuran, dimethylsulfoxide, hexamethylphosphoramide, benzene, toluene, xylene, etc., in the presence of a halogen scavenger and base, e.g., silver oxide.

The final compound can be separated and purified by conventional techniques, e.g., chromatography.

The compounds should be protected from light.

EXAMPLE 1

11β,17-Dihydroxy-6α-methyl-21-[(o-nitrobenzyl)-oxy]-pregna-1,4-diene-3,20-dione

6α-Methylprednisolone (1.86 g., 5 mmole) is dissolved in 20 ml. of dry dimethylformamide (distilled from calcium hydride). This is placed under nitrogen and silver oxide (1.3 g., 5.5 mmole), o- nitrobenzyl bromide (2.65 g., 12 mmole) and N,N-diisopropylethyl amine (2.5 ml.) are added with stirring. The mixture is heated to 50° C. for one hour and more silver oxide (1.3 g.) and o-nitrobenzyl bromide (2.65 g.) are added and the reaction continued for 5.5 hours. The reaction mixture is poured into 200 ml. of ethyl acetate and diluted with 100 ml of brine. After shaking, the organic layer is separated, dried over sodium sulfate and concentrated in vacuo. The residue is chromatographed on 400 g. of silica gel using 40% ethyl acetate-hexane (600 ml.) followed by 60% ethyl acetate-hexane. Fractions with Rf value 0.5–0.65 as determined by thin layer chromatography (85% ethyl acetate-hexane) are recovered (1.2 g.) and rechromatographed using 40% ethyl acetate-hexane on 150 g. silica gel column. The fractions with Rf=0.60 are recovered to give 450 mg. of 11β,17-dihydroxy-6α-methyl-21-[(o-nitrobenzyl)oxy]-pregna-1,4-diene-3,20-dione as a light yellow solid and having a melting point of 116°–119° C. (unrecrystallized).

Analysis:

Calc'd. for $C_{29}H_{35}NO_7$: C, 68.35; H, 6.92; N, 2.75. Found: C, 69.30; H, 7.33; N, 2.81.

EXAMPLE 2

11β,17-Dihydroxy-9α-fluoro-16α-methyl-21-[(o-nitrobenzyl)oxy]pregna-1,4-diene-3,20-dione Following the procedure of Example 1 but substituting 9α-fluoro-11β,17α,21-trihydroxy-16α-methyl-1,4-pregnadiene-3,20-dione for the 6α-methylprednisolone there is obtained 11β,17α-dihydroxy-9α-fluoro-16α-methyl-21-[(o-nitrobenzyl)-oxy]pregna-1,4-diene-3,20-dione as a light yellow solid of m.p. 102°–106° C. (unrecrystallized).

Analysis:

Calc'd. for $C_{29}H_{34}FNO_7$:C, 66.02; H, 6.50; N, 2.65. Found: C, 64.58; H, 6.55; N, 2.81.

EXAMPLE 3

11β,17-dihydroxy-6α-methyl-21-[(3,4-dimethoxy-6-nitrobenzyl)oxy]-pregna-1,4-diene-3,20-dione Following the procedure of Example 1 but substituting 3,4-dimethoxy-6-nitrobenzyl bromide for the o-nitrobenzyl bromide and increasing the reaction period to 40 hours there is obtained 11β,17-dihydroxy-6α-methyl-21-[(3,4-dimethoxy-6-nitrobenzyl)oxy]pregna-1,4-diene-3,20-dione as a yellow solid.

In the manner given in Examples 1–3 other steroids of the formula Ib can be prepared starting with compounds of formula Ia where R is hydrogen. Representative compounds, there obtained, include:

11β,17α-dihydroxy-6α-methyl-21[(2-nitro-4-chlorobenzyl)oxy]-pregna-1,4-diene-3,20-dione, 11β,17α-dihydroxy-6α-methyl-21-[(2-nitro-3-bromobenzyl)oxy]-pregna-1,4-diene-3,20-dione, 11β,17α-dihydroxy-6α-methyl-21-[(4,5-dichloro-2-nitro benzyl)oxy]-pregna-1,4-diene-3,20-dione, 11β,17α-dihydroxy-6α-methyl-21-[(4-methoxy-2-nitrobenzyl)oxy]-pregna-1,4-diene-3,20-dione, 11β,17α-dihydroxy-6α-methyl-9α-fluoro-21-[(o-nitrobenzyl)oxy]-pregna-1,4-diene-3,20-dione, 11β,17α-dihydroxy-6α,9α-difluoro-21-[(2-nitro-4,5-dimethoxybenzyl)oxy]-pregna-1,4-diene-3,20-dione, 17α-hydroxy-9α,11β-dichloro-6α-methyl-21-[(o-nitrobenzyl)oxy]-pregna-1,4-3,20-dione, 17α-hydroxy-11-keto-6α-methyl-16-fluoro-21-[(o-nitrobenzyl)oxy]-pregna-1,4-diene-3,20-dione, 11β,16α,17α- trihydroxy-6α-chloro-9α-fluoro-16,17-acetonide-21-[(4-chloro-2-nitrobenzyl)oxy]-pregna-1,4-diene-3,20-dione, 11β-hydroxy-9α-chloro-16α-methyl-21-[(o-nitrobenzyl)-oxy]-pregna-4-ene-3,20-dione, 6α-fluoro-9α,11β-dichloro-16α,17α-dihydroxy-16,17-acetonide-21-[(o-nitrobenzyl)oxy]-pregna-4-ene-3,20-dione, 6α,9-difluoro-11β,17-dihydroxy-16β-methyl-21-[(o-nitrobenzyl)oxy]-pregna-1,4-diene-3,20-dione, 6α,9-difluoro-11β,17-dihyroxy-16β-methyl-17-acetoxy-<-[(o-nitrobenzyl)oxy]-pregna-1,4-diene-3,20-dione, 11β,17-dihydroxy-9α-fluoro-16α-methyl-21-[(2-nitro-4-methoxybenzyl)oxy]-pregna-1,4-diene-3,20-dione, 11β,16,17-trihydroxy-6α-methyl-9α-fluoro-21- 8 (2-nitro-4-chlorobenzyl)oxy]-pregna-1,4-diene,-3,20-dione, 11β,17-dihydroxy-6α,16α-dimethyl-21[(2-nitro-4-chloro-5-methoxybenzyl)oxy]-pregna-1,4-diene-3,20-dione, 11β,17-dihydroxy-6α,16α-dimethyl-9α-fluoro-21[(o-nitrobenzyl)oxy]-pregna-1,4-diene-3,20-dione.

EXAMPLE 4

11β,17α-Dihydroxy-6α-metyl-21-[(o-nitrobenzyl)-oxycarbonyl]oxy-pregna-1,4-diene-3,20-dione To 6α-methylprednisolone (5.58 g., 15 mmole) in 75 ml. of dry pyridine under nitrogen at room temperature, with stirring, is added o-nitrobenzyloxycarboxyl chloride (4.30 g., 20 mmole) dropwise over 5 minutes. The reaction is allowed to stirr for 16 hours and the 200 ml. of ethyl acetate and 100 ml. of water are added. The organic phase is separated and washed once with 100 ml. of 0.1 N hydrochloric acid, followed by brine, dried over sodium sulfate and concentrated in vacuo. The residue is chromatographed on 200 g. silica gel column using 70% ethyl acetate-hexane and recrystallized from ethyl acetate to give 11β,17α-dihydroxy-6α-methyl-21-[(o-nitrobenzyl)oxycarbonyl]oxy-pregna-1,4-diene-3,20-dione of m.p. 198°–199° C.

Analysis: Calc'd. for $C_{30}H_{35}NO_9$: C, 65.08; H, 6.37; N, 2.53. Found: C, 64.95; H, 6.44; N, 2.41.

EXAMPLE 5

11β,17-Dihydroxy-9α-fluoro-16α-methyl-21-[(o-nitrobenzyl]oxycarbonyl]oxy-pregna-1,4-diene-3,20-dione Following the procedure of Example 4 but substituting 11β,17,21-trihydroxy-9α,-fluroro-16α-methylpregna-1,4-diene-3,20-dione for the 6α-methylprednisolone there is obtained 11β,17-dihyroxy-9α-fluoro-16α-methyl-21[(o-nitrobenzyl)-oxycarbonyl]oxy-pregna-1,4-diene-3,20-dione of m.p. 203°–204° C. (recrystallized twice from acetone).

Analysis: Calc'd. for $C_{30}H_{34}FNO_9$: C, 63.04; H, 6.00; N, 2.45. Found: C, 62.19; H, 6.03; N, 2.52.

EXAMPLE 6

9α-Fluoro-21-[(o-nitrobenzyl)oxycarbonyl]oxy-11β, 16, 17- trihydroxypregna-1,4-diene-3,20-dione Following the procedure of Example 4 but substituting 11β,16α,17α,21-tetrahydroxy-9α-fluoropregna-1,4-diene-3,20-dione for 6α-methylprednisolone there is obtained 9α-fluoro-21-[(o-nitrobenzyl)oxycarbonyl]oxy-11β,16α,17α-trihydroxypregna-1,4-diene-3,20-dione of m.p. 205°–207° C.

Analysis: Calc'd. for $C_{29}H_{32}FNO_{10}$: C, 60.72; H, 5.62; N, 2.44. Found: C, 59.58; H, 5.48; N, 2.63.

In the manner given in Examples 4–6 other steroids of the formula I can be prepared from compounds of formula II wherein R is hydrogen. Representative compounds, thus obtained, include:

11β,17α-dihydroxy-6α-methyl-21-[(2-nitro-4,5-dimethoxybenzyl)oxycarbonyl]oxy-pregna-1,4-diene-3,20-dione, 11β,17α- dihydroxy-6α,16α-dimethyl-9α,fluoro-21-(o-nitrobenzyl)oxycarbonyl]oxy-pregna-1,4-diene-3,20-dione, 9α,11β-dichloro-6α-metyl-16α,17α-dihydroxy-21-[(2-nitro-3-bromobenzyl)oxycarbonyl]oxy-pregna-1,4-diene-3,20-dione 16,17-acetonide, 6α,9α,-difluoro-11β,16α,17α-trihydroxy-21[(o-nitrobenzyl)oxycarbonyl]oxy-pregna-1,4-diene-3,20-dione, 6α,9α-difluoro-11β,17α-dihydroxy-16β-methyl-21-[(o-nitrobenzyl)oxycarbonyl]oxy-pregna-1,4-diene-3,20-dione 17-acetate, 6α,9α-dichloro-11-keto-21-[(3,4-dichloro-2-nitrobenzyl)oxycarbonyl]oxy-pregna-1,4-diene-3,20-dione, 11β,17-dihydroxy-6α-methyl-21-[(o-nitrobenzyl)oxycarbonyl]oxy-pregna-4-ene-3,20-dione, 6α-methyl-9α-chloro-11β,16α,17α-trihydroxy-16,17-acetonide-21-[(3-bromo-4-chloro-2-nitrobenzyl)oxycarbonyl]oxy-pregna-1,4-diene-3,20-dione, 9α-fluoro-11β-hydroxy-21-[(o-nitrobenzyl)oxycarbonyl]oxy-pregna-1,4-diene-3,20-dione, 6α,9-difluoro-11β,17-dihydroxy-16β-methyl-21-[(o-nitrobenzyl)oxycarbonyl]oxy-pregna-4-ene-3,20-dione, 6α,9α-difluoro-16-chloro-11β,17α-dihydroxy-21-[(2-nitro-3,6-dibromobenzyl)oxycarbonyl]oxy-pregna-1,4-diene-3,20-dione, 6α,16α-dimethyl-9α,11β-dichloro-17α-hydroxy-21-[(o-nitrobenzyl)oxycarbonyl]oxy-pregna-1,4-diene-3,20-dione 17-acetate, 6α,9α,16-trifluoro-21- [(o-nitrobenzyl)oxycarbonyl]oxy-pregna-1,4-diene-3,11,20-trione, 9α-fluoro-11β,16α,17α-trihydroxy-21-[(o-nitrobenzyl)oxycarbonyl]oxy-pregna-1,4-diene-3,20-dione 16,17-acetonide.

EXAMPLE 7

$N^6$-butyryl-2'-(o-nitrobenzyl)-3',5'-cyclic adenosine monophosphate (IIb)

$N^6$-Butyryl-3',5'-cyclic adenosine monophosphate (IIa) ($R_1$, Z and Y are H; $R_4$ is OH; and $R_2$ is butyryl) and o-nitrobenzyl bromide are substituted for A and reagent a, respectively, in procedure 1. When the reaction is complete as judged by TLC, the product is isolated by addition of ethyl acetate and saturated sodium bicarbonate. The aqueous phase is separated, acidified to pH approximately 4 and extracted several times with ethyl acetate. The combined organic phases are dried over sodium sulfate and concentrated in vacuo to give a residue. The residue, containing the product is purified by chromatography, particularly ion exchange chromatography, to afford $N^6$-butyryl-2'-(o-nitrobenzyl)-3',5'-cyclic adenosine monophosphate (IIb).

Substituting other compounds of formula IIa for $N^6$-butyryl-2'-(o-nitrobenzyl)-3',5'-cyclic adenosine monophosphate and substituting other reagents of formula

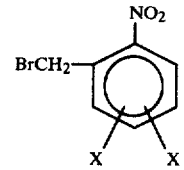

where X is H, methoxy, chloro and bromo for o-nitrobenzylbromide there are produced other products of formula IIb.

Alternatively, starting with $N^6$-butyryladenosine, and applying the procedure of Ohtsuka et al., Nucleic Acids Research 1, 1351 (1974), followed by the procedure of Smith et al., J. Am. Chem. Soc. 83, 698 (1961), the same product can be obtained.

EXAMPLE 8

A compound of formula IIb wherein $R_2$ is o-nitrobenzyl, R is H, Y is H, and Z is H, benzylthio or alkylthio is prepared by the procedure of example 7 starting with IIa where R, Y and Z are as defined above and $R_2$ is H, limiting the amount of o-nitrobenzylbromide to 2 equivalents.

EXAMPLE 9

A compound of formula IIb wherein $R_2$ is o-nitrobenzyloxycarbonyl, R is H, Y is H and Z is H, benzylthio or alkylthio is prepared from IIa where $R_2$ is H and R, Y and Z are as defined above by substituting IIa for A and o-nitrobenzyloxycarbonyl chloride for reagent f in procedure 5.

EXAMPLE 10

A product of formula IIb in which both $R_2$ and R are o-nitrobenzyl is prepared starting with IIa in which $R_2$ and R are H and with o-nitrobenzylbromide in the procedure of example 7.

EXAMPLE 11

A product of formula VIIIb in which R is isobutyl, $R_1$ is methyl, $R_2$ is H, and Y is o-nitrobenzyl is prepared by substituting VIIIa wherein R, $R_2$ and $R_3$ are as defined above and Y is OH for B and o-nitrobenzylbromide for reagent a in procedure 1. Substituting other compounds of formula VIIIa and other reagents of formula

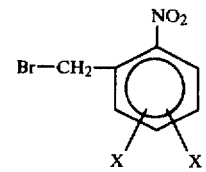

where X is H, methoxy, chloro and bromo for o-nitrobenzylbromide, there are produced other products of formula VIIIb.

Alternatively, procedure 7 may be used with VIIIa and reagent b to produce VIIIb.

EXAMPLE 12

A product of formula VIIIb in which Y is

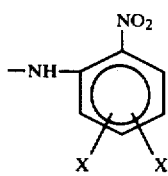

is produced by substituting VIIIa for B and

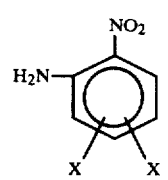

for reagent c in procedure 6. Similarly, using reagent g in the same procedure affords VIIIb wherein Y is

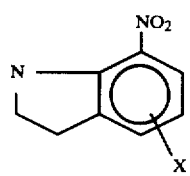

EXAMPLE 13

A product of formula IXb wherein Y is OH and Z is o-nitrobenzyl is prepared by substituting 5 mM of IXa (methotrexate) for A and 25 mM of o-nitrobenzylbromide (reagent a) in procedure 1. The thus obtained intermediate of formula IXb wherein Y is o-nitrobenzyloxy and Z is o-nitrobenzyl is saponified with dilute sodium carbonate. The saponified material is acidified and purified to afford IXb where Y is OH and Z is o-nitrobenzyl. Other products of formula IXb wherein Y is OH and Z is

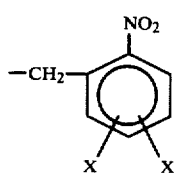

are produced using other reagents of formula a.

EXAMPLE 14

A product of formula IXb wherein Y is OH and Z is o-nitrobenzyloxycarbonyl is prepared by substituting 5 mM of IXa for A and 12 mM of o-nitrobenzyloxycarbonyl chloride for reagent f in procedure 5. Similarly, substituting other reagents of formula

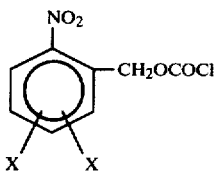

for o-nitrobenzyloxycarbonyl chloride there are produced other products of formula IXb.

EXAMPLE 15

A product of formula Xb wherein $R_1$, $R_2$, $R_3$ and $R_4$ are H, $R_5$ is carbonyl, and $R_6$ is o-nitrobenzyl is produced by substituting Xa wherein $R_1$, $R_2$, $R_3$, $R_4$ and $R_5$ are as defined above and $R_6$ is H (cycloheximide) and o-nitrobenzyl bromide for A and reagent a, respectively in procedure 1.

Substituting other materials of formula Xa and other reagents of the formula

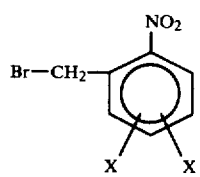

in the above procedure affords other products of formula Xb.

EXAMPLE 16

A product of formula Xb wherein $R_1$, $R_2$, $R_3$ and $R_6$ are H, $R_5$ is carbonyl, and $R_4$ is o-nitrobenzyloxycarbonyl is prepared by substituting cycloheximide for A and o-nitrobenzyloxycarbonyl chloride for reagent f in procedure 5. Substituting other materials of Xa and other reagents of formula

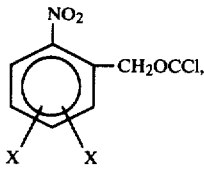

there are produced other products of formula Xb.

EXAMPLE 17

A compound of formula XIb wherein R is o-nitrobenzyl is prepared by substituting XIa (indomethacin) for A and o-nitrobenzylbromide for reagent a in procedure 1. Use of other reagents of formula

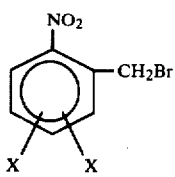

affords other products of formula XIb. Alternatively, procedure 7 may be used with XIa and reagent b to produce XIb.

EXAMPLE 18

A compound of formula XIb wherein R is

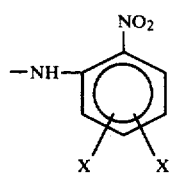

is prepared by substituting indomethacin for B and o-nitroaniline for reagent c in procedure 6. Substituting reagent g or other examples of reagent c in the same procedure affords other compounds of formula XIIb.

EXAMPLE 19

A compound of formula XIIb wherein R is o-nitrobenzyl and $R_1$ is H is prepared by substituting XIIa where R is OH and $R_1$ is H for B and o-nitrobenzyl alcohol for reagent b in procedure 7. Similarly substituting other reagents of formula

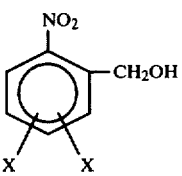

for o-nitrobenzyl alcohol affords other products of formula XIIb ($R_1$ is H).

EXAMPLE 20

A compound of formula XIIb wherein R is

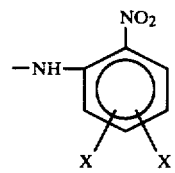

and $R_1$ is H is prepared by substituting XIIa for B and o-nitroaniline for reagent c in procedure 6.

Similarly, substituting other reagents of formula

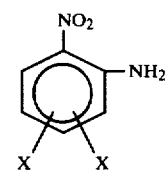

or reagent g, there are produced other products of formula XIIb.

EXAMPLE 21

A compound of formula XXIIIb wherein $R_1$, $R_2$ and $R_5$ are H, $R_3$ is methoxy; $R_4$ is n-butyloxy; and $R_6$ is o-nitro benzyl is prepared by substituting 5 mM of XXIIIa wherein $R_1-R_5$ are as defined above and $R_6$ is H for A and 5.5 mM of o-nitrobenzyl bromide for reagent a in procedure 1. Similarly, using 10 mM of o-nitrobenzylbromide, there is obtained a mixture of XXIIIb wherein $R_1-R_6$ are as defined above, XXIIIb wherein $R_1-R_4$ is as defined above, $R_6$ is H and $R_5$ is o-nitrobenzyl and XXIIIb wherein $R_1-R_4$ is as defined above and $R_5$ and $R_6$ are o-nitrobenzyl. Said mixture can be separated by chromatography to give the purified products. Substituting other reagents of formula

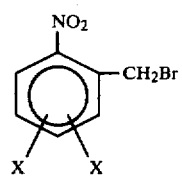

for o-nitrobenzyl bromide produces other products of formula XXIIIb.

EXAMPLE 22

A compound of formula XXVb wherein $R_2$ is o-nitrobenzyl and $R_1$ is H is prepared by substituting XXVa wherein $R_1$ and $R_2$ are H (5-fluorouracil) for A and o-nitrobenzylbromide for reagent a in procedure 1. Increasing the amount of o-nitrobenzyl bromide to 12 mM affords XXVb wherein $R_1$ and $R_2$ are o-nitrobenzyl. Substituting the 2-o-trimethylsilyl derivative (see Niedball and H. Vorbrüggen, *J. Org. Chem.* 41, 2084 (1976) for general procedures) of 5-fluorouracil affords XXVb where $R_1$ is o-nitrobenzyl and $R_2$ is H. Substituting other reagents of formula

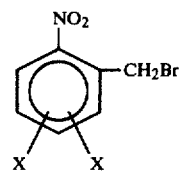

for o-nitrobenzylbromide affords other products of formula XXVb.

EXAMPLE 23

A compound of formula XXVIIb wherein R is

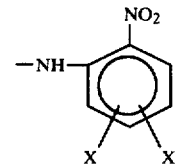

is prepared from XXVIIa, R is OH (retinoic acid) by substituting XXVIIa for B and o-nitroaniline for reagent c in procedure 6. Substituting other reagents of formula

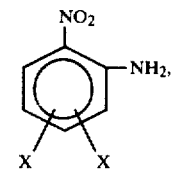

or reagent g, affords other products of formula XXVIIb.

EXAMPLE 24

A compound of formula XXIVb wherein $R_1$ is o-nitrobenzyl is prepared by heating N-methylurethane with o-nitrobenzyloxyamine in benzene under reflux and azeotroping out the ethanol so produced. When the reaction is complete as determined by TLC, the mixture is concentrated to dryness and the residue, containing the product, is purified by chromatography. In like manner, substituting

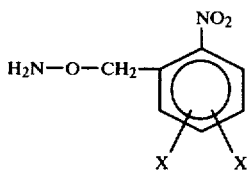

where X is H, methoxy, chloro and bromo for o-nitrobenzyloxyamine, there are produced other products of formula XXIVb wherein $R_1$ is

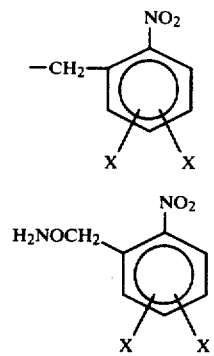

is prepared from acetone oxime and reagent a by methods known in the art (e.g., by procedure 1 followed by hydrolysis with acid).

EXAMPLE 25

A compound of formula XXIVb wherein $R_1$ is o-nitrobenzyl, $R_2$ and $R_3$ are H, is prepared from o-nitrobenzyloxyamine (0.1 M) in water containing 6 N hydrochloric acid to which is added gradually a solution of potassium cyanate in water. When the reaction is complete, as determined by TLC, brine is added and the product isolated by extraction in chloroform. The solvent is evaporated to dryness and the product purified by chromatography.

EXAMPLE 26

A compound of formula XXIVb wherein $R_3$ is o-nitrobenzyl and $R_1$ and $R_2$ are H is prepared from o-nitrobenzylamine by reaction with ethylchloroformate in a solvent containing one equivalent of pyridine. Suitable solvents are benzene and tetrahydrofuran. When the reaction is complete, brine is added and the product, N-(o-nitrobenzyl)-O-ethyl carbamate, is isolated by extraction. To the thus obtained carbamate in a solvent such as benzene or dioxane is added at least one equivalent of hydroxylamine hydrochloride and an equivalent amount of a tertiary amine such as triethylamine or pyridine. The mixture is warmed until the reaction is complete, as determined by TLC. The reaction mixture is concentrated to a small volume, diluted with brine, and extracted with chloroform. The product is isolated by evaporation to dryness and purified by chromatography to afford essentially pure N-(o-nitrobenzyl)hydroxy urea, XXIVb, wherein $R_3$ is o-nitrobenzyl and $R_1$ and $R_2$ are H. Substituting other reagents of formula

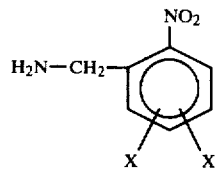

wherein X is H, methoxy, chloro and bromo, for o-nitrobenzylamine produces other products of formula XXIVb wherein $R_1$ and $R_2$ are H and $R_3$ is

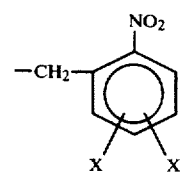

EXAMPLE 27

A reagent of formula

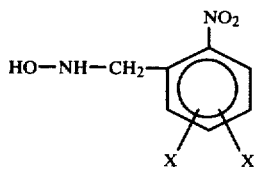

where X is H, methoxy, chloro and bromo [e.g., N-(o-nitrobenzyl)hydroxylamine)] is prepared from hydroxylamine by methods well known in the art (e.g., from hydroxylamine and reagent a by the process of procedure 1). The thus obtained reagent is substituted for o-nitrobenzyloxyamine in the process of example 24 to produce the product of formula XXIVb wherein $R_1$ and $R_3$ are H and $R_2$ is

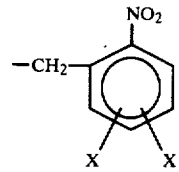

EXAMPLE 28

A product of formula XXIVb as defined below is produced by substituting 1 equivalent of hydroxy urea for A and using 2.5 equivalents of reagent f (e.g., o-nitrobenzyloxycarbonyl chloride) in procedure 5. The reaction product is isolated as described in procedure 5, dissolved in methanol, and treated with aqueous sodium bicarbonate for 2 hours. After neutralization with dilute hydrochloric acid, the solvent is evaporated and the residue extracted with chloroform and chromatographed to give purified XXIVb wherein $R_3$ is o-nitrobenzyloxycarbonyl chlorocarbonate, and $R_1$ and $R_2$ are H, and a small amount of XXIVb wherein $R_2$ is o-nitrobenzyloxycarbonyl and $R_1$ and $R_3$ are H.

EXAMPLE 29

A product of formula XXVIIIb wherein $R_1$ and $R_2$ are H and R is

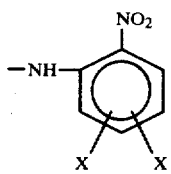

is prepared from XXVIIIa wherein $R_1$ and $R_2$ are H, R is methoxy (α-methylornithine methyl ester) by heating XXVIIIa in benzene containing ten equivalents of o-nitroaniline and azeotroping of the methanol thus produced until the reaction is complete as determined by TLC. The product is recovered by evaporation to a residue. The product may be purified by adsorption or ion-exchange chromatography to afford XXVIIIb. In like manner, other products of formula XXVIIIb wherein R is

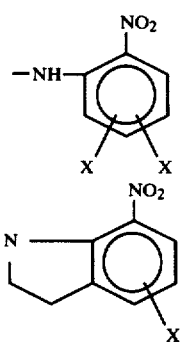

are produced.

EXAMPLE 30

A product of formula XXVIIIb wherein $R_1$ and $R_2$ are H and R is

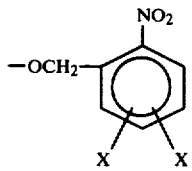

is produced from a substance of formula XXVIIIa wherein $R_1$ and $R_2$ are H and $R_3$ is OH by Fischer esterification, using an excess of

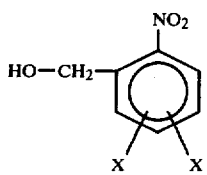

(e.g., o-nitrobenzyl alcohol) and 3-5 equivalents of gaseous hydrogen chloride in an inert solvent (e.g., dioxane).

EXAMPLE 31

A product of formula XXVIIIb wherein $R_1$ is

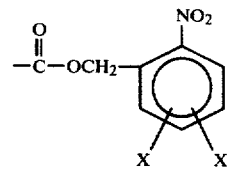

(e.g., o-nitrobenzyloxycarbonyl), $R_2$ is H and R is OH is produced by substituting α-methylornithine for A in procedure 5 but replacing pyridine with water containing 4 equivalents of $NaHCO_3$. There is also produced a small amount of XXVIIIb wherein $R_1$ and $R_2$ are both

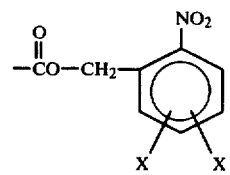

and R is OH. The thus obtained products can be separated by ion exchange and acid-washed silica gel chromatography.

EXAMPLE 32

A product of formula XXVIIIb wherein $R_1$ is o-nitrobenzyl, $R_2$ is H and R is methoxy is obtained by substituting XXVIIIa wherein $R_1$ and $R_2$ are H and R is methoxy for A and o-nitrobenzylbromide for reagent a in the process of procedure 1. Chromatographic separation of the products thus produced affords XXVIIIb as defined above and a small amount of XXVIIIb wherein $R_1$ is H, $R_2$ is o-nitrobenzyl and R is $OCH_3$. Substituting other reagents a for o-nitrobenzylbromide affords other products of formula XXVIIIb. Saponification of XXVIIIb with sodium hydroxide in aqueous methanol affords XXVIIIb wherein R is OH and $R_1$ and $R_2$ are as defined above.

EXAMPLE 33

A product of the formula XXIXb wherein $R_1$ and $R_2$ are H and R is

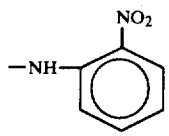

is produced by substituting 5-amino-2-hydrazino-3-pentanoic acid methyl ester for α-methyl ornithine methyl ester in the procedure of example 29. In like manner, other products of formula XXIXb are produced using other reagents of formula

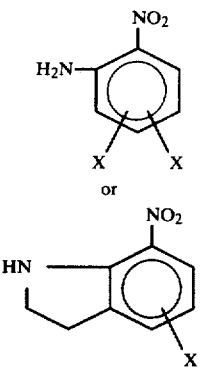

EXAMPLE 34

Products of formula XXIXb wherein R₁ is o-nitrobenzyloxycarbonyl, R₂ is H and R₃ is OH; R₁ is H, R₂ is o-nitrobenzyloxycarbonyl, and R₃ is OH; and R₁, R₂ are o-nitrobenzyloxycarbonyl and R₃ is OH are produced by substituting 5-amino-2-hydrazino-2-methylpentanoic acid for α-methylornithine in the procedure of example 29. Other products of formula XXIXb are similarly produced using

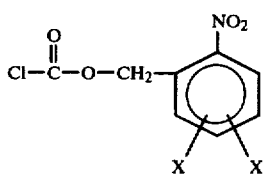

in place of o-nitrobenzyloxycarbonyl chloride.

EXAMPLE 35

Products of the formula XXIXb wherein R₁ is o-nitrobenzyl, R₂ is H and R is OCH₃, wherein R₁ is H, R₂ is o-nitrobenzyl and R is OCH₃, and wherein both R₁ and R₂ are o-nitrobenzyl are produced by substituting 5-amino-2-hydrazino-2-methylpentanoic acid methyl ester for A and o-nitrobenzylbromide for reagent a in the process of procedure 1. The products are separated by ion-exchange chromatography. Substituting other reagents a for o-nitrobenzylbromide affords other products of formula XXIXb. Saponification of XXIXb with sodium hydroxide in aqueous methanol affords XXIXb wherein R is OH and R₁ and R₂ are as defined above.

EXAMPLE 36

Products of formula XXXb wherein R₁ is o-nitrobenzyl and R₂ is H, and wherein R₁ is H and R₂ is o-nitrobenzyl are produced by substituting methylglyoxal bis-guanylhydrazone for A in the process of procedure 1 using o-nitrobenzylbromide for reagent a. The thus obtained products are separated and purified by chromatography. In like manner, using other reagents of formula

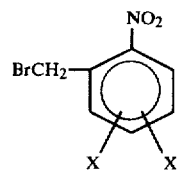

there are produced other products of formula XXXb.

EXAMPLE 37

Products of formula XXXb wherein R₁ is o-nitrobenzyloxycarbonyl and R₂ is H and wherein R₁ is H and R₂ is o-nitrobenzyloxycarbonyl are produced by substituting methylglyoxal bis-guanylhydrazone for A and using o-nitrobenzyloxycarbonyl chloride for reagent f in the process of procedure 5. Using other reagents of formula f there are produced other products of formula XXXb.

EXAMPLE 38

A product of formula IXb wherein Z is H and Y is

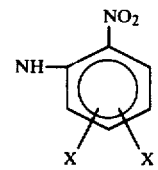

(e.g., X is H) is prepared by protecting a compound of formula IXa wherein Z is H and Y is OH (methotrexate) as its bis-phthalimide or bis-t-butyloxycarbonyl derivative by the methods of Nefkins (*Nature* 309, 1960) or McKay and Albertson (J. Am. Chem. Soc. 79, 4686, 1957). The thus protected methotrexate derivatives are substituted for C in procedure 3 and the protecting groups are then removed according to the above cited references or by the method of McOhmie. Adv. Org. Chem. 3, 191, 1963 to afford product IXb wherein Z is H and Y is

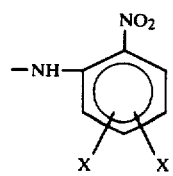

(e.g., X is H). By substituting

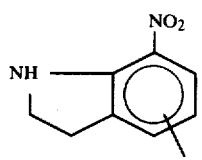

for

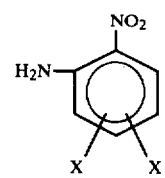

other products of formula IXb are obtained. Similarly, by substituting

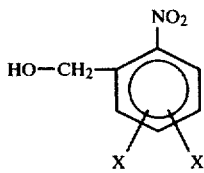

for

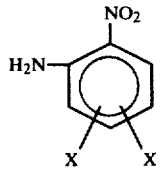

compounds of formula IXb wherein Z is H and Y is

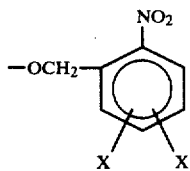

are obtained.

EXAMPLE 39

A product of formula Xb wherein $R_1$, $R_2$, $R_3$ and $R_6$ are H, $R_5$ is carbonyl and $R_4$ is o-nitrobenzyl is prepared by gently warming a solution of Xa wherein $R_1$, $R_2$, $R_3$, $R_5$ and $R_6$ are as defined above and $R_4$ is OH in an inert solvent with an excess of o-nitrobenzyl alcohol. If desired, a trace of acid or base such as p-toluenesulfonic acid or triethylamine may be employed. Similarly, other substances of formula Xa treated with other alcohols of formula

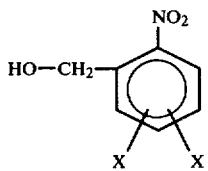

afford other products of formula Xb.

EXAMPLE 40

Substituting other materials of formulas Ia-XXXIa and reagents a-g in the appropriate procedures 1-9 there are produced other products of formulas Ib-XXIb.

The quantity of the pro-drug to be used in the compositions of this invention for administration topically, parenterally or systemically ranges from about 0.1% to about 15% weight/volume topically; from about 0.1% to about 10% w/v parenterally; and for oral dosage forms the % amount of active ingredient is determined by the physical characteristics of the carrier with regard to manufacturing requirements and elegance.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule or appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacanth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration the dosage forms are prepared utilizing the active compound or compounds and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compositions of this invention, from 1 to 10 times usual dosage of the cleaved active compound can be employed.

The therapeutically active form of the compound as released at the desired site of action by irradiation with ultraviolet light, i.e., light having a wave length of from about 2500 to 400 angstroms, a preferred range is from about 3100 to 3700 angstroms and especially preferred is a range of from 3500 to 3600 angstroms. The intensity of the irradiation can be from 1 to 40 joules/cm$^2$ of skin area with an intensity of 3–20 joules/cm$^2$ of skin preferred in a single exposure or repeated several times daily.

The pro-drugs can be used to treat all the diseases that the cleaved compounds are known to be useful to treat, particularly those disease conditions which are of a dermatological nature, including, but not limited to, proliferative skin diseases.

The expression "proliferative skin diseases" mean benign and proliferative skin diseases which are characterized by epidermal cell proliferation, or division, and may also be associated with incomplete tissue differentiation. Psoriasis is the most serious of the skin diseases with which this invention is concerned. Such diseases include: psoriasis, atopic dermatitis, non-specific dermatitis, primary irritant contact dermatitis, allergic contact dermatitis, lamellar ichthyosis, epidermolytic hyperkeratosis, premalignant sun induced keratosis, non-malignant keratosis, and seborrheic dermatitis in humans and atopic dermatitis and mange in domesticated animals.

EXAMPLE 41

Tablets

Ten thousand tablets for oral use are prepared from the following types and amounts of material:

| | |
|---|---|
| 11β,17-dihydroxy-9α-fluoro-16α-methyl-21-[(o-nitrobenzyl)oxy]-pregna-1,4-diene-3,20-dione | 25 gm. |
| Lactose | 900 gm. |
| Corn starch | 125 gm. |
| Magnesium stearate | 10 gm. |
| Light liquid petrolatum | 25 gm. |

The ingredients are thoroughly mixed and slugged. The slugs are broken down by forcing through a number sixteen screen. The resulting granules are then compressed into tablets, each tablet containing 2.5 mg. of 11β,17-dihydroxy-9α-fluoro-16α-methyl-21-[(o-nitrobenzyl)oxy]-pregna-1,4-diene-3,20-dione.

The foregoing tablets are useful for systemic treatment of psoriasis in adult humans by oral administration of 1 tablet every 4 hours followed by irradiation of the psoriatic lesions with 1 joule/cm$^2$.

EXAMPLE 42

Parenteral solution

A sterile aqueous solution for intramuscular use, containing in 1 cc. 5 mg. of 11β,17-dihydroxy-6α-methyl-21-[(3,4-dimethoxy-6-nitrobenzyl)oxy]-pregna-1,4-diene-3,20-dione is prepared from the following types and amounts of materials:

| | |
|---|---|
| 11β,17-dihydroxy-6α-methyl-21-[(3,4-dimethoxy-6-nitrobenzyl)oxy]-pregna-1,4-diene-3,20-dione | 5 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day followed by irradiation of the psoriatic lesions with 20 joules/cm$^2$.

EXAMPLE 43

Parenteral solution

A sterile aqueous solution for intradermal use, containing in 1 cc. 5 mg. of 11β,17-dihydroxy-6α-methyl-21-[(o-nitrobenzyl)oxy]-pregna-1,4-diene-3,20-dione is prepared from the following types and amounts of ingredients:

| | |
|---|---|
| 11β,17-dihydroxy-6α-methyl-21-[(o-nitrobenzyl)oxy]-pregna-1,4-diene-3,20-dione | 5 gm. |
| Sodium chloride 10% solution q.s. | |
| Water for injection q.s. | 1000 cc. |

The 11β,17-dihydroxy-6α-methyl-21-[(o-nitrobenzyl)oxy]-pregna-1,4-diene-3,20-dione is added to the water and sufficient sodium chloride added to form an isotonic solution and the solution sterilized by filtration.

The sterile solution is administered intradermally by high pressure injection for treatment of psoriasis and the area irradiated with 40 joules/cm$^2$.

EXAMPLE 44

Cream

One thousand grams of a topical cream are prepared from the following types and amounts of ingredients:

| | |
|---|---|
| 11β,17-dihydroxy-6α-methyl-21-[(o-nitrobenzyl)oxy]-pregna-1,4-diene-3,20-dione | 90 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70°–80° C. The methylparagen is dissolved in about 500 gm. of water and the propylene glycol, polysorbate 80, and 11β,17-dihydroxy-6α-methyl-21-[(o-nitrobenzyl)oxy]-pregna-1,4-diene-3,20-dione are added in turn, maintaining a temperature of 75°-80° C. The methylparaben mixture is added slowly to the Tegacid and spermaceti melt, with constant stirring. The addition is continued for at least 30 minutes with continued stirring until the temperature has dropped to 40°-45° C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

The foregoing composition is useful for the treatment of psoriasis by applying to the lesions with occlusive bandage for six hours followed by removal of the bandage and cream and irradiation of the area with 10 joules/cm$^2$.

EXAMPLE 45

Following the procedure of the preceding Examples 41 to 43, inclusive, substituting an equimolar amount of
11β,17α-dihydroxy-6α-methyl-21-[(o-nitrobenzyl)oxy]-pregna-1,4-diene-3,20-dione,
11β,17α-dihydroxy-9α-fluoro-16α-methyl-21-[(o-nitrobenzyl)oxy]-pregna-1,4-diene-3,20-dione,
11β,17α-dihydroxy-6α-methyl-21-[(3,4-dimethoxy-6-nitrobenzyl)oxy]-pregna-1,4-diene-3,20-dione,
11β,17α-dihydroxy-6α-methyl-21-[(o-nitrobenzyl)oxycarbonyl]-pregna-1,4-diene-3,20-dione,
11β,17α-dihydroxy-9α-fluoro-16α-methyl-21-[(o-nitrobenzyl)oxycarbonyl]oxy-pregna-1,4-diene-3,20-dione,
9α-fluoro-21-o-[(o-nitrobenzyl)oxycarbonyl]oxy-11β,16α,17α-trihydroxypregna-1,4-diene-3,20-dione,
6α,9-difluoro-11β,17-dihydroxy-16β-methyl-21-[(o-nitrobenzyl)oxy]-pregna-1,4-diene-3,20-dione,
6α,9-difluoro-11β,17-dihydroxy-16β-methyl-21-[(o-nitrobenzyl)oxycarbonyl]oxy-pregna-1,4-diene-3,20-dione for the 11β,17-dihydroxy-6α-methyl-21-[(o-nitrobenzyl)oxy]-pregna-1,4-diene-3,20-dione composition are similarly prepared and used.

EXAMPLE 46

Following the procedure of the preceding Examples 41 through 43, inclusive, the compositions are used in the treatment of atopic dermatitis, non-specific dermatitis, primary irritant dermatitis, allergic contact dermatitis, lamellar ichthyosis, epidermolytic hyperkeratosis, premalignant sun induced keratosis, non-malignant keratosis, or seborrheic dermatitis in humans and atopic dermatitis in animals.

EXAMPLE 46

Capsules

One thousand two-piece hard gelatin capsules for oral use, each containing 200 mg. of N$^6$-butyryl-2'-(o-nitrobenzyl)-3',5'-cyclicadenosine monophosphate (hereinafter N$^6$-butyryl-2'-(o-nitrobenzyl) cAMP, IIb) are prepared from the following types and amounts of materials:

| | |
|---|---|
| N$^6$-butyryl-2'-(o-nitrobenzyl)-cAMP | 200 gm. |
| Corn starch | 150 gm. |
| Talc | 75 gm. |
| Magnesium stearate | 2.5 gm. |

The materials are thoroughly mixed and then encapsulated in the usual manner.

The foregoing capsules are useful for the systemic treatment of psoriasis in adult humans by the oral administration of 1 capsule every 4 hours and irradiation of the lesions with 5 joules/cm$^2$.

Using the procedure above, capsules are similarly prepared containing in 5, 100, and 500 mg. amounts by substituting 5, 100, and 500 gm. of N$^6$-butyryl-2'-(o-nitrobenzyl) cAMP for the 200 gm. used above.

EXAMPLE 47

One thousand two-piece hard gelatin capsules for oral use each containing 200 mg. of N$^6$-butyryl-2'-o-nitrobenzyl-8-methylthio-3',5'-cyclic adenosine monophosphate (hereinafter N$^6$-butyryl-2'-o-nitrobenzyl-8-methylthio cAMP, IIb) are prepared from the following types and amounts of materials:

| | |
|---|---|
| N$^6$-butyryl-2'-o-nitrobenzyl-8-methylthio cAMP | 200 gm. |
| Corn starch | 250 gm. |
| Talc | 75 gm. |
| Magnesium stearate | 2.5 gm. |

The ingredients are thoroughly mixed and then encapsulated in the usual manner.

The foregoing capsules are useful for the systemic treatment of psoriasis in adult humans by the oral administration of 1 capsule twice a day and irradiation of the lesions with 10 joules/cm$^2$.

EXAMPLE 48

Tablets

One thousand tablets for oral use, each containing 500 mg. 2-(p-isobutylphenyl)propionic acid o-nitroanilino amide (VIIIb) are prepared from the following types and amounts of materials:

| | |
|---|---|
| 2-(p-isobutylphenyl)propionic acid o-nitroanilino amide | 500 gm. |
| Lactose | 125 gm. |
| Corn starch | 65 gm. |
| Magnesium stearate | 7.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing 500 mg. of 2-(p-isobutylphenyl)propionic acid o-nitroanilino amide.

The foregoing tablets are useful for systemic treatment of psoriasis in adult humans by oral administration of 1 tablet every 4 hours and irradiation of the lesions with 10 joules/cm$^2$.

EXAMPLE 49

Oral syrup

One thousand cc. of an aqueous suspension for oral use, containing in each 5 cc. dose 100 mg. of 1-(3,4-dihydroxyphenyl)-1-[(o-nitrobenzyl)oxycarbonyloxy]-2-t- butylaminoethane (VIIb) is prepared from the following types and amounts of ingredients:

| | |
|---|---|
| 1-(3,4-dihydroxyphenyl)-1-[(o-nitrobenzyl)oxycarbonyloxy]-2-t-butylaminoethane | 20 gm. |
| Citric acid | 2 gm. |
| Benzoic acid | 1 gm. |
| Sucrose | 700 gm. |
| Tragacanth | 5 gm. |
| Lemon oil | 2 cc. |
| Deionized water q.s. | 1000 cc. |

The citric acid, benzoic acid, sucrose, tragacanth, and lemon oil are dispersed in sufficient water to make 850 cc. of solution. The pro-drug is stirred into the syrup until uniformly distributed. Sufficient water is added to make 1000 cc.

The composition prepared is useful in the systemic treatment of psoriasis in adult humans at a dose of 1 teaspoonful 4 times a day and irradiation with 10 joules/cm$^2$.

EXAMPLE 50

Parenteral solution

A sterile aqueous solution for intramuscular use, containing in 1 cc. 75 mg. of 4-(o-nitrobenzyloxycarbonylamino)-N$^{10}$-methylpteroylglutamic acid (IXb) is prepared from the following types and amounts of materials:

| | |
|---|---|
| 4-[(o-nitrobenzyl)oxycarbonylamino]-10-methyl folic acid | 75 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day and irradiation with 20 joules/cm$^2$.

EXAMPLE 51

Topical ointment

One thousand gm. of 0.25% ointment is prepared from the following types and amounts of ingredients:

| | |
|---|---|
| 3-[2-(3,5-dimethyl-2-oxo-cyclohexyl)-2-(o-nitrobenzyloxy)ethyl]glutarimide (Xb) | 2.5 gm. |
| Liquid petrolatum (heavy) | 250 gm. |
| Wool fat | 200 gm. |
| White petrolatum q.s. | 1000 gm. |

The white petrolatum and wool fat are melted and 100 gm. of liquid petrolatum added thereto. The active ingredient is added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to the skin of animals for the treatment of mange. The ointment is removed after 4 hours and the skin irradiated with 20 joules/cm$^2$.

EXAMPLE 52

Cream

One thousand grams of a topical cream are prepared from the following types and amounts of ingredients:

| | |
|---|---|
| 7-(o-nitrobenzyl)-1,3-dimethylxanthine (XVb) | 50 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*self-emulsifying glyceryl monostearate from Goldschmidt Chemical Corporation, New York, N. Y.

The Tegacid and spermaceti are melted together at a temperature of 7°–80° C. The methylparaben is dissolved in about 500 gm. of water and the propylene glycol, polysorbate 80, and active ingredient are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by adding 2.5 gm. of citric acid and 0.2 gm. of dibasic sodium phosphate dissolved in about 50 gm. of water. Finally sufficient water is added to bring the final weight to 1000 gm. and the preparation stirred to maintain homogeneity until cooled and congealed.

The foregoing composition is useful for the treatment of psoriasis by applying to the lesions with occlusive bandage. The bandage is removed after 12 hours and the lesion irradiated with 20 joules/cm$^2$.

EXAMPLE 53

The compositions prepared in the preceding Examples 46 to 52, inclusive, can similarly be administered for treatment of atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

EXAMPLE 54

By substituting other materials of formula Ib-XXXIb in appropriate pharmaceutical dosage form as exemplified in Examples 41–44 and 46–52, inclusive, there are obtained compositions which can be administered for treatment of atopic dermatitis, non-specific dermatitis, primary irritant contact dermatitis, allergic contact dermatitis, basal and squamous cell carcinomas of the skin, lamellar ichthyosis, epidermolytic hyperkeratosis, pre-malignant sun induced keratosis, non-malignant keratosis, acne, and seborrheic dermatitis in humans and atopic dermatitis and mange in domesticated animals in conjunction with phototherapy.

We claim:

1. A process for treating a dermatological disease which comprises:
   (a) administering to a human or animal afflicted with a dermatological disease a composition comprising a pro-drug in combination with a pharmaceutical carrier, and (b) irradiating the diseased area with radiation having a wave length of from about 2500 to about 3600 angstroms in an amount sufficient to convert said administered pro-drug to a pharmaceutically active form and in a concentration effective to alleviate the said disease and the pro-drug is a compound of the formula:

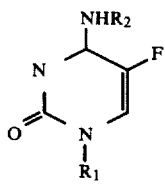　XXVIb wherein $R_1$ is H or

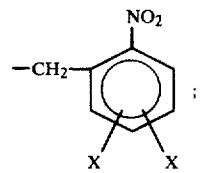

$R_2$ is H,

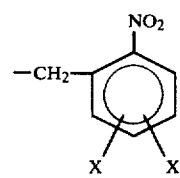

or

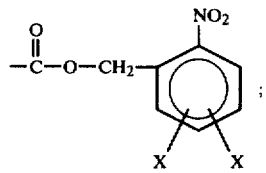

and X is H, methoxy, chloro or bromo, provided that one of the groups $R_1$ and $R_2$ is not H.

UNITED STATES PATENT OFFICE
CERTIFICATE OF CORRECTION

Patent No. 4,302,457                               Dated  November 24, 1981

Inventor(s)  John J. Voorhees and Wendell Wierenga

It is certified that error appears in the above-identified patent and that said Letters Patent are hereby corrected as shown below:

Column 32, line 10, "1,4-3,20-" should read -- 1,4-diene-3,20- --.
Column 32, line 24, " <-[(o-" should read -- 21-[(o- --.
Column 32, line 27, "21- 8 (2-" should read -- 21-[(2- --.
Column 32, line 37, "metyl" should read -- methyl --.
Column 32, line 47, "of0.1" should read -- of 0.1 --.
Column 33, line 10, "oxycarbony]" should read -- oxycarbonyl] --.
Column 33, line 22, "-(o-" should read -- -[(o- --.
Column 41, line 35, " and" should be inserted.

Signed and Sealed this

Ninth Day of July 1985

[SEAL]

Attest:

DONALD J. QUIGG

Attesting Officer          Acting Commissioner of Patents and Trademarks